United States Patent
Hondmann et al.

(10) Patent No.: US 9,289,461 B2
(45) Date of Patent: Mar. 22, 2016

(54) REDUCING THE RISK OF AUTOIMMUNE DISEASE

(71) Applicant: Mead Johnson Nutrition (Asia Pacific) Pte. Ltd., Singapore (SG)

(72) Inventors: Dirk Hondmann, Winnetka, IL (US); Eric A. F. van Tol, Arnhem (NL); Gabriele Gross, Nijmegen (NL); Marieke H. Schoemaker, Rhenen (NL); Teartse Tim Lambers, Nijmegen (NL)

(73) Assignee: Mead Johnson Nutrition Company, Glenview, IL (US)

( * ) Notice: Subject to any disclaimer, the term of this patent is extended or adjusted under 35 U.S.C. 154(b) by 0 days.

(21) Appl. No.: 13/839,212

(22) Filed: Mar. 15, 2013

(65) Prior Publication Data

US 2014/0274892 A1   Sep. 18, 2014

(51) Int. Cl.
*A61K 38/01* (2006.01)

(52) U.S. Cl.
CPC .................................... *A61K 38/018* (2013.01)

(58) Field of Classification Search
None
See application file for complete search history.

(56) References Cited

U.S. PATENT DOCUMENTS

| | | |
|---|---|---|
| 3,876,766 A | 4/1975 | Frommer et al. |
| 3,937,817 A | 2/1976 | Frommer et al. |
| 4,016,260 A | 4/1977 | Karasaki et al. |
| 4,358,465 A | 11/1982 | Brule et al. |
| 4,361,587 A | 11/1982 | Brule et al. |
| 4,491,589 A | 1/1985 | Dell et al. |
| 4,902,501 A | 2/1990 | Bandi et al. |
| 5,102,871 A | 4/1992 | Furukawa et al. |
| 5,112,812 A | 5/1992 | Samuelsson et al. |
| 5,230,902 A | 7/1993 | Gold et al. |
| 5,308,832 A | 5/1994 | Garleb et al. |
| 5,405,637 A * | 4/1995 | Martinez et al. ............ 426/580 |
| 5,605,893 A | 2/1997 | Kaufman |
| 5,643,880 A | 7/1997 | Mukerji et al. |
| 5,714,472 A | 2/1998 | Gray et al. |
| 5,723,446 A | 3/1998 | Gray et al. |
| 5,821,217 A | 10/1998 | Forse et al. |
| 6,077,558 A | 6/2000 | Euber |
| 6,180,761 B1 | 1/2001 | Han et al. |
| 6,451,368 B1 | 9/2002 | Elliot et al. |
| 6,451,552 B1 | 9/2002 | van Beresteijn et al. |
| 6,468,962 B1 | 10/2002 | Portman |
| 6,495,344 B1 | 12/2002 | Carr et al. |
| 6,713,082 B2 | 3/2004 | van Loon et al. |
| 6,875,456 B2 | 4/2005 | Delest et al. |
| 6,905,702 B1 | 6/2005 | Kaufman |
| 7,022,676 B2 | 4/2006 | Tamura et al. |
| 7,091,320 B2 | 8/2006 | Pozzilli et al. |
| 7,214,521 B2 | 5/2007 | Wada et al. |
| 7,258,996 B2 | 8/2007 | Jullerat et al. |
| 7,501,490 B2 | 3/2009 | Kadowaki et al. |
| 7,550,436 B2 | 6/2009 | Takahashi et al. |
| 7,563,458 B2 | 7/2009 | Kume et al. |
| 7,579,315 B2 | 8/2009 | Smith et al. |
| 7,629,744 B2 | 12/2009 | Ahn et al. |
| 7,648,721 B2 | 1/2010 | Edens et al. |
| 7,648,957 B2 | 1/2010 | Heyden et al. |
| 7,666,996 B2 | 2/2010 | Sidelman |
| 7,741,274 B2 | 6/2010 | Sidelman |
| 7,785,824 B2 | 8/2010 | van der Burg-Koorevaar et al. |
| 7,972,808 B2 | 7/2011 | Edens et al. |
| 8,119,142 B2 | 2/2012 | Zwijsen et al. |
| 8,129,337 B2 | 3/2012 | Wolfram |
| 8,273,710 B2 | 9/2012 | Boots |
| 8,343,531 B2 | 1/2013 | Morifuji et al. |
| 8,354,502 B2 | 1/2013 | Recio Sanchez et al. |
| 8,367,614 B2 | 2/2013 | Hatori et al. |
| 8,859,210 B2 | 10/2014 | Valenta et al. |
| 2002/0147144 A1 | 10/2002 | Sidelman |
| 2003/0138476 A1 | 7/2003 | van Leeuwen et al. |
| 2004/0063633 A1 | 4/2004 | Hayasawa et al. |
| 2004/0180380 A1 | 9/2004 | Lee et al. |
| 2005/0019372 A1 | 1/2005 | Corkey et al. |
| 2005/0089969 A1 | 4/2005 | Wissler et al. |
| 2005/0148504 A1 | 7/2005 | Katunuma et al. |
| 2006/0234942 A1 | 10/2006 | Tauzin et al. |
| 2007/0060519 A1 | 3/2007 | Rozing et al. |
| 2007/0098762 A1 | 5/2007 | Stahl et al. |
| 2007/0203060 A1 | 8/2007 | Sidelman et al. |

(Continued)

FOREIGN PATENT DOCUMENTS

| | | |
|---|---|---|
| CA | 2340223 | 2/2000 |
| DE | 102004040452 | 2/2006 |

(Continued)

OTHER PUBLICATIONS

MedlinePlus, Autoimmune Disorders, U.S. National Library of Medicine, accessed on Jan. 23, 2014).*
Alles et al. Current trends in the composition of infant milk formulas (Current Paediatrics (2004) 14, 51-63).*
http://www.medscape.com/viewarticle/449854, Dooley et al. published 2003.*
Akuzawa et al (Chapter 8, "Bioactive Components in Caseins, Caseinates, and Cheeses" in Bioactive Components in Milk and Dairy Products, edited by Park (2009) Wiley-Blackwell).*
Ebner et al., "Nonallergic individuals recognize the same T cell epitopes of Bet v 1, the major birch pollen allergen, as atopic patients," J. Immunol. 1995, vol. 154, pp. 1932-1940.

(Continued)

*Primary Examiner* — James H Alstrum Acevedo
*Assistant Examiner* — Tara Martinez
(74) *Attorney, Agent, or Firm* — Patterson Intellectual Property Law, P.C; James R. Cartiglia; Bethany J. Whelan

(57) ABSTRACT

The present disclosure provides a method for reducing the risk of autoimmune disease by administering a composition comprising peptides selected from a casein hydrolysate. Such a composition, may reduce the symptoms of autoimmune disease and may be a treatment for autoimmune disease, especially type 1 diabetes. Preferably, the hydrolysate consists of peptides with a molecular weight of more than 500 Da.

10 Claims, 9 Drawing Sheets

(56) References Cited

U.S. PATENT DOCUMENTS

| | | | |
|---|---|---|---|
| 2008/0031814 | A1 | 2/2008 | Hageman |
| 2008/0075828 | A1 | 3/2008 | Wolfram et al. |
| 2008/0096794 | A1 | 4/2008 | Boehm et al. |
| 2008/0108548 | A1 | 5/2008 | Luyer et al. |
| 2006/0587324 | | 6/2008 | Geerlings et al. |
| 2008/0132454 | A1 | 6/2008 | Geerlings et al. |
| 2008/0221023 | A1 | 9/2008 | Boots |
| 2008/0226565 | A1 | 9/2008 | Huybrechts |
| 2009/0036351 | A1 | 2/2009 | Boots |
| 2009/0074893 | A1 | 3/2009 | de Waard et al. |
| 2009/0075904 | A1 | 3/2009 | Boots |
| 2009/0123605 | A1 | 5/2009 | van Benthum et al. |
| 2009/0131331 | A1 | 5/2009 | Edens et al. |
| 2009/0203592 | A1 | 8/2009 | Beerman et al. |
| 2009/0252729 | A1 | 10/2009 | Farrington et al. |
| 2009/0305945 | A1 | 12/2009 | Wolfram et al. |
| 2009/0318366 | A1 | 12/2009 | Edens et al. |
| 2009/0325888 | A1 | 12/2009 | Edens et al. |
| 2010/0047393 | A1 | 2/2010 | Glas et al. |
| 2010/0099607 | A1 | 4/2010 | Chen |
| 2010/0143262 | A1 | 6/2010 | Valenta |
| 2010/0256235 | A1 | 10/2010 | Puder et al. |
| 2010/0306864 | A1 | 12/2010 | Tsuji et al. |
| 2011/0177044 | A1 | 7/2011 | Thomas et al. |
| 2011/0190215 | A1* | 8/2011 | Kruzel ..................... 514/17.7 |
| 2011/0195153 | A1 | 8/2011 | Valenta et al. |
| 2012/0071400 | A1 | 3/2012 | Serizawa et al. |
| 2012/0142588 | A1 | 6/2012 | Rozing et al. |
| 2012/0322726 | A1 | 12/2012 | Somoto et al. |

FOREIGN PATENT DOCUMENTS

| | | |
|---|---|---|
| EP | 0274939 | 7/1988 |
| EP | 0448511 | 9/1991 |
| EP | 0629350 | 12/1994 |
| EP | 0418593 | 3/1997 |
| EP | 0791357 | 8/1997 |
| EP | 2017283 | 1/2009 |
| EP | 2332428 | 6/2011 |
| WO | 9111918 | 8/1991 |
| WO | 9212711 | 8/1992 |
| WO | 9802165 | 1/1998 |
| WO | 0137850 | 5/2001 |
| WO | 0219832 | 3/2002 |
| WO | 2005027953 | 3/2005 |
| WO | 2005081628 | 9/2005 |
| WO | 2005117933 | 12/2005 |
| WO | 2006068480 | 6/2006 |
| WO | 2007060421 | 5/2007 |
| WO | 2007064208 | 6/2007 |
| WO | 2008004794 | 1/2008 |
| WO | 2008054192 | 5/2008 |
| WO | 2008056983 | 5/2008 |
| WO | 2008108651 | 9/2008 |
| WO | 2008153429 | 12/2008 |
| WO | 2009033737 | 3/2009 |
| WO | 2010043724 | 4/2010 |
| WO | 2010125192 | 11/2010 |
| WO | 2011031149 | 3/2011 |
| WO | 2011069042 | 6/2011 |
| WO | 2012143362 | 10/2012 |

OTHER PUBLICATIONS

Elsayed et al., "T cell recognition pattern of bovine milk αS1-casein and its peptides," Mol. Immunol. 2004, vol. 41 (12), pp. 1225-1234.
Hirahara et al., K., Profound immunological tolerance in the antibody response against bovine alpha s1-casein induced by intradermal administration of a dominant T cell determinant,: Clinical Immunology and Immunophathology, vol. 76, No. 1, 1995, pp. 12-18.
Knip, M., et al., "Dietary Intervention in Infancy and Later Signs of Beta-Cell Autoimmunity," N Engl J Med 2010;363:1900-8.
Kondo et al., "The Response of bovine beta-lactoglobulin-specific T-cell clones to single amino acid substitution of T-cell core epitope," Pediatr. Allergy Immunol. 2008, vol. 19, pp. 592-598.
Nakajima-Adachi et al., "Determinant analysis of IgE and IgG4 antibodies and T cells specific for bovine αS1-casein from the same patients allergic to cow's milk: Existence of αS1-casein-specific B cells and T cells characteristic in cow's-milk allergy," J. Allergy Clin. Immunol. 1998; vol. 101(5), pp. 660-671).
Rosendal et al., "Detection of Potentially Allergenic Material in 12 Hydrolyzed Milk Formulas," Journal of Dairy Science 2000, vol. 83, No. 10, abstract.
Ruiter et al., "Characterization of T cell epitopes in αs1-casein in cow's milk allergic, atopic and non-atopic children," Clin. Exp. Allergy 2006, vol. 36(3), pp. 303-310.
Ruiter et al., "Role of Human Leucocyte Antigen DQ in the Presentation of T Cell Epitopes in the Major Cow's Milk Allergen αs1-casein," Int. Arch. Allergy Immunol. 2007; vol. 143(2), pp. 119-126.
Schmidt-Weber et al., "T-cell tolerance in allergic response," Allergy 2002, vol. 57, pp. 762-768.
Schulmeister et al., "Cloning, Expresion, and Mapping of Allergenic Determinants of αS1-Casein, a Major Cow's Milk Allergen," J Immunol. 2009, vol. 182(11), pp. 7019-7029.
Database WPI Wek 200022 Thompson Scientific, London, GB; AN 2000-251451.
Visser, J., et al., "Potential mechanisms explaining why hydrolyzed casein-based diets outclass single amino acid-based diets in the prevention of autoimmune diabetes in diabetes-prone BB rats," Diabetes Metab Res Rev 2012;28:505-513.
Visser, J., et al., "Restoration of impaired intestinal barrier function by hydrolysed casein diet contributes to the prevention of type 1 diabetes in the diabetes-prone BioBreeding rat," Diabetologia (2010) 53:2621-2628.
Brody, E., "Biological activities of bovine glycomacropeptide," British Journal of Nutrition (2000), 84, Suppl. 1, S39-S46.
Brugman, S., et al., "Neonatal oral administration of DiaPep277, combined with hydrolyzed casein diet, protects against Type 1 diabetes in BB-DP rats. An experimental study," Diabetologia, vo. 47, No. 7, Jan. 1, 2004.
Espeche Turbay, M.D., et al., "B-Casein hydrolysate generated by the cell envelope-associated proteinase of *Lactobacillus delbrueckii* ssp. Lactis CRL 581 protects against trinitrobenzene sulfonic acid-induced colitis in mice," J. Dairy Sci. 95:1108-1118.
Fiedorowicz, E., et al., "The influence of U-opioid receptor agonist and antagonist peptides on peripheral blood mononuclear cells (PMBCs)," Peptides 32 (2011) 707-712.
Hotta (Arterioscler Thromb Vasc Biol (Jun. 2000) 20: 1595-1599.
Knip, M., et al., "Dietary Intervention in Infancy and Later Signs of Beta-Cell Autoimmunity," New England Journal Medicine, vol. 363, pp. 1900-1908, Jan. 1, 2010.
Mao, X.Y., et al., "Free-radical-scavenging and anti-inflammatory effect of yak milk casein before and after enzymatic hydrolysis," Food Chemistry, vol. 126, No. 2, May 15, 2011.
Meisel, H., et al., "Bioactive peptides encrypted in milk proteins: proteolytic activation and thropho-functional properties," Antonie van Leenwenhqek 76:207-215, 1999.
Nakamura, Y., et al., "Metabolic diseases and pro- and prebiotics: Mechanistic insights," Nutrition & Metabolism 2012, 9:60.
Nielsen, D., et al., "Effect of milk hydrolysates on inflammation markers and drug-induced transcriptional alterations in cell-based models," J Anim Sci 2012, 90:403-405.
Peptide Protein Calculator, http://www.basic.northwestern.edu/biotools/proteincalc.html; downloaded on Nov. 18, 2014.
Requena, P., et al., "Bovine glycomacropeptide ameliorates experimental rat ileitis by mechanisms involving down regulation of interleukin 17," British Journal of Pharmacology (2008) 154, 825-832.
Sampson, H.A., Bernhisel-Broadbent, J., Yang, E., and Scanlon, S.M. Safety of casein hydrolysate formula in children with cow milk allergy. J. Pediatr. 1991; 118: 520-525.
Xue-Ying, M., et al., "Free-radical-scavenging and anti-inflammatory effect of yak milk casein before and after enzymatic hydrolysis," Food Chemistry 126 (2011) 484-490.
Wielinga, P., et al., "Arachidonic acid/docosahexaenoic acid-supplemented diet in early life reduces body weight gain, plasma lipids, and adiposity in later life in ApoE*3Leiden mice," Mol. Nutr. Food Res. 2012, 56, 1081-1089.

* cited by examiner

SEQUENCE LISTING

```
<160> NUMBER OF SEQ ID NOS: 68

<210> SEQ ID NO 1
<211> LENGTH: 6
<212> TYPE: PRT
<213> ORGANISM: BOVINE

<400> SEQUENCE: 1

Ile Pro Asn Pro Ile Gly
1               5

<210> SEQ ID NO 2
<211> LENGTH: 9
<212> TYPE: PRT
<213> ORGANISM: BOVINE

<400> SEQUENCE: 2

Ile Gly Ser Glu Ser Thr Glu Asp Gln
1               5
```

```
<210> SEQ ID NO 3
<211> LENGTH: 7
<212> TYPE: PRT
<213> ORGANISM: BOVINE

<400> SEQUENCE: 3

Asp Lys Thr Glu Ile Pro Thr
1               5

<210> SEQ ID NO 4
<211> LENGTH: 4
<212> TYPE: PRT
<213> ORGANISM: BOVINE

<400> SEQUENCE: 4

Ile Val Pro Asn
1

<210> SEQ ID NO 5
<211> LENGTH: 6
<212> TYPE: PRT
<213> ORGANISM: BOVINE

<400> SEQUENCE: 5

Leu Glu Asp Ser Pro Glu
1               5

<210> SEQ ID NO 6
<211> LENGTH: 6
<212> TYPE: PRT
<213> ORGANISM: BOVINE

<400> SEQUENCE: 6

Asn Gln Glu Gln Pro Ile
1               5

<210> SEQ ID NO 7
<211> LENGTH: 5
<212> TYPE: PRT
<213> ORGANISM: BOVINE

<400> SEQUENCE: 7

Asn Val Pro Gly Glu
1               5

<210> SEQ ID NO 8
<211> LENGTH: 6
<212> TYPE: PRT
<213> ORGANISM: BOVINE

<400> SEQUENCE: 8

Pro Phe Pro Gly Pro Ile
1               5

<210> SEQ ID NO 9
<211> LENGTH: 5
<212> TYPE: PRT
<213> ORGANISM: BOVINE

<400> SEQUENCE: 9

Thr Glu Asp Glu Leu
1               5

<210> SEQ ID NO 10
```

```
<211> LENGTH: 4
<212> TYPE: PRT
<213> ORGANISM: BOVINE

<400> SEQUENCE: 10

Val Pro Ser Glu
1

<210> SEQ ID NO 11
<211> LENGTH: 6
<212> TYPE: PRT
<213> ORGANISM: BOVINE

<400> SEQUENCE: 11

Tyr Pro Phe Pro Gly Pro
1               5

<210> SEQ ID NO 12
<211> LENGTH: 5
<212> TYPE: PRT
<213> ORGANISM: BOVINE

<400> SEQUENCE: 12

Tyr Pro Ser Gly Ala
1               5

<210> SEQ ID NO 13
<211> LENGTH: 6
<212> TYPE: PRT
<213> ORGANISM: BOVINE

<400> SEQUENCE: 13

Phe Pro Gly Pro Ile Pro
1               5

<210> SEQ ID NO 14
<211> LENGTH: 11
<212> TYPE: PRT
<213> ORGANISM: BOVINE

<400> SEQUENCE: 14

Met His Gln Pro His Gln Pro Leu Pro Pro Thr
1               5                   10

<210> SEQ ID NO 15
<211> LENGTH: 9
<212> TYPE: PRT
<213> ORGANISM: BOVINE

<400> SEQUENCE: 15

Tyr Pro Phe Pro Gly Pro Ile Pro Asn
1               5

<210> SEQ ID NO 16
<211> LENGTH: 5
<212> TYPE: PRT
<213> ORGANISM: BOVINE

<400> SEQUENCE: 16

Asp Met Glu Ser Thr
1               5

<210> SEQ ID NO 17
<211> LENGTH: 7
<212> TYPE: PRT
```

```
<213> ORGANISM: BOVINE

<400> SEQUENCE: 17

Phe Pro Gly Pro Ile Pro Asn
1               5

<210> SEQ ID NO 18
<211> LENGTH: 5
<212> TYPE: PRT
<213> ORGANISM: BOVINE

<400> SEQUENCE: 18

Ile Pro Asn Pro Ile
1               5

<210> SEQ ID NO 19
<211> LENGTH: 6
<212> TYPE: PRT
<213> ORGANISM: BOVINE

<400> SEQUENCE: 19

Met Glu Ser Thr Glu Val
1               5

<210> SEQ ID NO 20
<211> LENGTH: 6
<212> TYPE: PRT
<213> ORGANISM: BOVINE

<400> SEQUENCE: 20

Pro Gly Pro Ile Pro Asn
1               5

<210> SEQ ID NO 21
<211> LENGTH: 8
<212> TYPE: PRT
<213> ORGANISM: BOVINE

<400> SEQUENCE: 21

Pro His Gln Pro Leu Pro Pro Thr
1               5

<210> SEQ ID NO 22
<211> LENGTH: 4
<212> TYPE: PRT
<213> ORGANISM: BOVINE

<400> SEQUENCE: 22

Pro Asn Pro Ile
1

<210> SEQ ID NO 23
<211> LENGTH: 7
<212> TYPE: PRT
<213> ORGANISM: BOVINE

<400> SEQUENCE: 23

Ser Lys Asp Ile Gly Ser Glu
1               5

<210> SEQ ID NO 24
<211> LENGTH: 8
<212> TYPE: PRT
<213> ORGANISM: BOVINE
```

<400> SEQUENCE: 24

Tyr Pro Phe Pro Gly Pro Ile Pro
1               5

<210> SEQ ID NO 25
<211> LENGTH: 8
<212> TYPE: PRT
<213> ORGANISM: BOVINE

<400> SEQUENCE: 25

Ala Ile Asn Pro Ser Lys Glu Asn
1               5

<210> SEQ ID NO 26
<211> LENGTH: 5
<212> TYPE: PRT
<213> ORGANISM: BOVINE

<400> SEQUENCE: 26

Ala Pro Phe Pro Glu
1               5

<210> SEQ ID NO 27
<211> LENGTH: 6
<212> TYPE: PRT
<213> ORGANISM: BOVINE

<400> SEQUENCE: 27

Asp Ile Gly Ser Glu Ser
1               5

<210> SEQ ID NO 28
<211> LENGTH: 4
<212> TYPE: PRT
<213> ORGANISM: BOVINE

<400> SEQUENCE: 28

Asp Met Pro Ile
1

<210> SEQ ID NO 29
<211> LENGTH: 4
<212> TYPE: PRT
<213> ORGANISM: BOVINE

<400> SEQUENCE: 29

Asp Val Pro Ser
1

<210> SEQ ID NO 30
<211> LENGTH: 3
<212> TYPE: PRT
<213> ORGANISM: BOVINE

<400> SEQUENCE: 30

Glu Asp Ile
1

<210> SEQ ID NO 31
<211> LENGTH: 3
<212> TYPE: PRT
<213> ORGANISM: BOVINE

<400> SEQUENCE: 31

Glu Leu Phe
1

<210> SEQ ID NO 32
<211> LENGTH: 3
<212> TYPE: PRT
<213> ORGANISM: BOVINE

<400> SEQUENCE: 32

Glu Met Pro
1

<210> SEQ ID NO 33
<211> LENGTH: 7
<212> TYPE: PRT
<213> ORGANISM: BOVINE

<400> SEQUENCE: 33

Glu Thr Ala Pro Val Pro Leu
1               5

<210> SEQ ID NO 34
<211> LENGTH: 4
<212> TYPE: PRT
<213> ORGANISM: BOVINE

<400> SEQUENCE: 34

Gly Pro Phe Pro
1

<210> SEQ ID NO 35
<211> LENGTH: 4
<212> TYPE: PRT
<213> ORGANISM: BOVINE

<400> SEQUENCE: 35

Gly Pro Ile Val
1

<210> SEQ ID NO 36
<211> LENGTH: 8
<212> TYPE: PRT
<213> ORGANISM: BOVINE

<400> SEQUENCE: 36

Ile Gly Ser Ser Ser Glu Glu Ser
1               5

<210> SEQ ID NO 37
<211> LENGTH: 9
<212> TYPE: PRT
<213> ORGANISM: BOVINE

<400> SEQUENCE: 37

Ile Gly Ser Ser Ser Glu Glu Ser Ala
1               5

<210> SEQ ID NO 38
<211> LENGTH: 6
<212> TYPE: PRT
<213> ORGANISM: BOVINE

<400> SEQUENCE: 38

Ile Asn Pro Ser Lys Glu
1               5

```
<210> SEQ ID NO 39
<211> LENGTH: 9
<212> TYPE: PRT
<213> ORGANISM: BOVINE

<400> SEQUENCE: 39

Ile Pro Pro Leu Thr Gln Thr Pro Val
1               5

<210> SEQ ID NO 40
<211> LENGTH: 4
<212> TYPE: PRT
<213> ORGANISM: BOVINE

<400> SEQUENCE: 40

Ile Thr Ala Pro
1

<210> SEQ ID NO 41
<211> LENGTH: 7
<212> TYPE: PRT
<213> ORGANISM: BOVINE

<400> SEQUENCE: 41

Lys His Gln Gly Leu Pro Gln
1               5

<210> SEQ ID NO 42
<211> LENGTH: 5
<212> TYPE: PRT
<213> ORGANISM: BOVINE

<400> SEQUENCE: 42

Leu Asp Val Thr Pro
1               5

<210> SEQ ID NO 43
<211> LENGTH: 5
<212> TYPE: PRT
<213> ORGANISM: BOVINE

<400> SEQUENCE: 43

Leu Pro Leu Pro Leu
1               5

<210> SEQ ID NO 44
<211> LENGTH: 5
<212> TYPE: PRT
<213> ORGANISM: BOVINE

<400> SEQUENCE: 44

Asn Ala Val Pro Ile
1               5

<210> SEQ ID NO 45
<211> LENGTH: 5
<212> TYPE: PRT
<213> ORGANISM: BOVINE

<400> SEQUENCE: 45

Asn Glu Val Glu Ala
1               5
```

```
<210> SEQ ID NO 46
<211> LENGTH: 3
<212> TYPE: PRT
<213> ORGANISM: BOVINE

<400> SEQUENCE: 46

Asn Leu Leu
1

<210> SEQ ID NO 47
<211> LENGTH: 5
<212> TYPE: PRT
<213> ORGANISM: BOVINE

<400> SEQUENCE: 47

Pro Ile Thr Pro Thr
1               5

<210> SEQ ID NO 48
<211> LENGTH: 6
<212> TYPE: PRT
<213> ORGANISM: BOVINE

<400> SEQUENCE: 48

Pro Asn Ser Leu Pro Gln
1               5

<210> SEQ ID NO 49
<211> LENGTH: 6
<212> TYPE: PRT
<213> ORGANISM: BOVINE

<400> SEQUENCE: 49

Pro Asn Ser Leu Pro Gln
1               5

<210> SEQ ID NO 50
<211> LENGTH: 7
<212> TYPE: PRT
<213> ORGANISM: BOVINE

<400> SEQUENCE: 50

Pro Gln Asn Ile Pro Pro Leu
1               5

<210> SEQ ID NO 51
<211> LENGTH: 6
<212> TYPE: PRT
<213> ORGANISM: BOVINE

<400> SEQUENCE: 51

Pro Val Leu Gly Pro Val
1               5

<210> SEQ ID NO 52
<211> LENGTH: 4
<212> TYPE: PRT
<213> ORGANISM: BOVINE

<400> SEQUENCE: 52

Pro Val Pro Gln
1

<210> SEQ ID NO 53
<211> LENGTH: 5
```

```
<212> TYPE: PRT
<213> ORGANISM: BOVINE

<400> SEQUENCE: 53

Pro Val Val Pro
1               5

<210> SEQ ID NO 54
<211> LENGTH: 6
<212> TYPE: PRT
<213> ORGANISM: BOVINE

<400> SEQUENCE: 54

Pro Val Val Val Pro Pro
1               5

<210> SEQ ID NO 55
<211> LENGTH: 11
<212> TYPE: PRT
<213> ORGANISM: BOVINE

<400> SEQUENCE: 55

Ser Ile Gly Ser Ser Ser Glu Glu Ser Ala Glu
1               5                   10

<210> SEQ ID NO 56
<211> LENGTH: 7
<212> TYPE: PRT
<213> ORGANISM: BOVINE

<400> SEQUENCE: 56

Ser Ile Ser Ser Ser Glu Glu
1               5

<210> SEQ ID NO 57
<211> LENGTH: 11
<212> TYPE: PRT
<213> ORGANISM: BOVINE

<400> SEQUENCE: 57

Ser Ile Ser Ser Ser Glu Glu Ile Val Pro Asn
1               5                   10

<210> SEQ ID NO 58
<211> LENGTH: 6
<212> TYPE: PRT
<213> ORGANISM: BOVINE

<400> SEQUENCE: 58

Ser Pro Pro Glu Ile Asn
1               5

<210> SEQ ID NO 59
<211> LENGTH: 7
<212> TYPE: PRT
<213> ORGANISM: BOVINE

<400> SEQUENCE: 59

Ser Pro Pro Glu Ile Asn Thr
1               5

<210> SEQ ID NO 60
<211> LENGTH: 7
<212> TYPE: PRT
<213> ORGANISM: BOVINE
```

```
<400> SEQUENCE: 60

Thr Asp Ala Pro Ser Phe Ser
1               5

<210> SEQ ID NO 61
<211> LENGTH: 6
<212> TYPE: PRT
<213> ORGANISM: BOVINE

<400> SEQUENCE: 61

Val Ala Thr Glu Glu Val
1               5

<210> SEQ ID NO 62
<211> LENGTH: 5
<212> TYPE: PRT
<213> ORGANISM: BOVINE

<400> SEQUENCE: 62

Val Leu Pro Val Pro
1               5

<210> SEQ ID NO 63
<211> LENGTH: 4
<212> TYPE: PRT
<213> ORGANISM: BOVINE

<400> SEQUENCE: 63

Val Pro Gly Glu
1

<210> SEQ ID NO 64
<211> LENGTH: 6
<212> TYPE: PRT
<213> ORGANISM: BOVINE

<400> SEQUENCE: 64

Val Pro Gly Glu Ile Val
1               5

<210> SEQ ID NO 65
<211> LENGTH: 6
<212> TYPE: PRT
<213> ORGANISM: BOVINE

<400> SEQUENCE: 65

Val Pro Ile Thr Pro Thr
1               5

<210> SEQ ID NO 66
<211> LENGTH: 9
<212> TYPE: PRT
<213> ORGANISM: BOVINE

<400> SEQUENCE: 66

Val Val Pro Pro Phe Leu Gln Pro Glu
1               5

<210> SEQ ID NO 67
<211> LENGTH: 5
<212> TYPE: PRT
<213> ORGANISM: BOVINE

<400> SEQUENCE: 67
```

```
Val Val Val Pro Pro
1               5

<210> SEQ ID NO 68
<211> LENGTH: 5
<212> TYPE: PRT
<213> ORGANISM: BOVINE

<400> SEQUENCE: 68

Tyr Pro Val Glu Pro
1               5
```

REDUCING THE RISK OF AUTOIMMUNE DISEASE

TECHNICAL FIELD

The present disclosure relates to a method for reducing autoimmune disease using peptides selected from a casein hydrolysate.

BACKGROUND ART

Autoimmune diseases arise from an inappropriate immune response of the body against substances and tissues normally present in the body. This may be restricted to certain organs (e.g. in autoimmune thyroiditis) or involve a particular tissue in different places (e.g. Goodpasture's disease which may affect the basement membrane in both the lung and the kidney). The treatment of autoimmune diseases is typically with immunosuppression medication that decreases the immune response.

Diabetes mellitus type 1 (type 1 diabetes, T1DM, formerly insulin dependent or juvenile diabetes) is a form of diabetes mellitus that results from autoimmune destruction of insulin-producing beta cells of the pancreas. The subsequent lack of insulin leads to increased blood and urine glucose. The classical symptoms are polyuria (frequent urination), polydipsia (increased thirst), polyphagia (increased hunger), and weight loss. Incidence varies from 8 to 17 per 100,000 in Northern Europe and the U.S. with a high of about 35 per 100,000 in Scandinavia to a low of 1 per 100,000 in Japan and China. Eventually, type 1 diabetes is fatal unless treated with insulin. Injection is the most common method of administering insulin although other methods are insulin pumps and inhaled insulin. Other alternatives are Pancreatic transplants that have been used and also pancreatic islet cell transplantation. Transplantation is experimental yet growing.

Celiac disease is an autoimmune disorder of the small intestine that occurs in genetically predisposed people of all ages from middle infancy onward. Symptoms include pain and discomfort in the digestive tract, chronic constipation and diarrhea, failure to thrive (in children), and fatigue, but these may be absent, and symptoms in other organ systems have been described. Vitamin deficiencies are often noted in people with Coeliac disease due to the reduced ability of the small intestine to properly absorb nutrients from food. Increasingly, diagnoses are being made in asymptomatic persons as a result of increased screening; the condition is thought to affect between 1 in 1,750 and 1 in 105 people in the United States. Coeliac disease is caused by a reaction to gliadin, a prolamin (gluten protein) found in wheat, and similar proteins found in the crops of the tribe Triticeae (which includes other common grains such as barley and rye). Upon exposure to gliadin, and specifically to three peptides found in prolamins, the enzyme tissue transglutaminase modifies the protein, and the immune system cross-reacts with the small-bowel tissue, causing an inflammatory reaction. That leads to a truncating of the villi lining the small intestine (called villous atrophy). This interferes with the absorption of nutrients, because the intestinal villi are responsible for absorption. The only known effective treatment is a lifelong gluten-free diet. While the disease is caused by a reaction to wheat proteins, it is not the same as wheat allergy HLA-DQ2 (DQ2) is a serotype group within HLA-DQ (DQ) serotyping system. The serotype is determined by the antibody recognition of $\beta^2$ subset of DQ β-chains. DQ2 represents the second highest risk factor for coeliac disease, the highest risk is a close family member with disease. Due to its link to coeliac disease, DQ2 has the highest association of any HLA serotype with autoimmune disease, close to 95% of all celiacs have DQ2, of that 30% have 2 copies of DQ2. Of the DQ2 homozygotes who eat wheat, lifelong risk is between 20 and 40% for coeliac disease. Juvenile diabetes (T1D) has a high association with DQ2.5 and there appears to be link between GSE and early onset male T1D. Anti-tTG antibodies are found elevated in a one-third of T1D patients, and there are indicators that Triticeae may be involved but the gluten protein is a type of globulin (Glb1). Recent studies indicate a combination of DQ2.5 and DQ8 (both acid peptide presenters) greatly increase the risk of adult onset Type 1 Diabetes and ambiguous type I/II Diabetes. HLA-DR3 plays a prominent role in autoimmune diabetes. However, DQ2 presence with DR3 decreases the age of onset and the severity of the autoimmune disorder.

HLA-DQ8 (DQ8) is a human leukocyte antigen serotype within the HLA-DQ (DQ) serotype group. DQ8 is a split antigen of the DQ3 broad antigen. DQ8 is determined by the antibody recognition of 68 and this generally detects the gene product of DQB1*0302. DQ8 is commonly linked to autoimmune disease in the human population. DQ8 is the second most predominant isoform linked to coeliac disease and the DQ most linked to juvenile diabetes. DQ8 increases the risk for rheumatoid arthritis and is linked to the primary risk locus for RA, HLA-DR4. DR4 also plays an important role in juvenile diabetes. While the DQ8.1 haplotype is associated with disease, there is no known association with the DQB1*0305, DQ8.4 or DQ8.5 haplotypes with autoimmune disease; however, this may be the result of lack of study in populations that carry these and the very low frequency. In Europe, DQ8 is associated with juvenile diabetes and coeliac disease. The highest risk factor for type 1 diabetes is the HLA DQ8/DQ2.5 phenotype. In parts of eastern Scandinavia both DQ2.5 and DQ8 are high increases frequencies of late onset Type I and ambiguous Type I/II diabetes. DQ8 is also found in many indigenous peoples of Asia, it was detected early on in the Bedoin population of Arabia where DQ2.5 is frequently absent, and in these instances DQ8 is solely associated HLA in Coeliac Disease.

Crohn's disease, also known as Crohn syndrome and regional enteritis, is a type of inflammatory bowel disease that may affect any part of the gastrointestinal tract from mouth to anus, causing a wide variety of symptoms. It primarily causes abdominal pain, diarrhea (which may be bloody if inflammation is at its worst), vomiting (can be continuous), or weight loss, but may also cause complications outside the gastrointestinal tract such as skin rashes, arthritis, inflammation of the eye, tiredness, and lack of concentration. Crohn's disease is caused by interactions between environmental, immunological and bacterial factors in genetically susceptible individuals. This results in a chronic inflammatory disorder, in which the body's immune system attacks the gastrointestinal tract possibly directed at microbial antigens. There is a genetic association with Crohn's disease, primarily with variations of the NOD2 gene and its protein, which senses bacterial cell walls. Siblings of affected individuals are at higher risk. Males and females are equally affected. Smokers are two times more likely to develop Crohn's disease than nonsmokers. Crohn's disease affects between 400,000 and 600,000 people in North America. Prevalence estimates for Northern Europe have ranged from 27-48 per 100,000. Crohn's disease tends to present initially in the teens and twenties, with another peak incidence in the fifties to seventies, although the disease can occur at any age. There is no known pharmaceutical or surgical cure for Crohn's disease.

Treatment options are restricted to controlling symptoms, maintaining remission, and preventing relapse.

Ulcerative colitis (Colitis ulcerosa, UC) is a form of inflammatory bowel disease (IBD). Ulcerative colitis is a form of colitis, a disease of the colon (large intestine), that includes characteristic ulcers, or open sores. The main symptom of active disease is usually constant diarrhea mixed with blood, of gradual onset. IBD is often confused with irritable bowel syndrome (IBS), a troublesome, but much less serious, condition. Ulcerative colitis has similarities to Crohn's disease, another form of IBD. Ulcerative colitis is an intermittent disease, with periods of exacerbated symptoms, and periods that are relatively symptom-free. Although the symptoms of ulcerative colitis can sometimes diminish on their own, the disease usually requires treatment to go into remission. Ulcerative colitis has an incidence of 1 to 20 cases per 100,000 individuals per year, and a prevalence of 8 to 246 per 100,000 individuals per year. The disease is more prevalent in northern countries of the world, as well as in northern areas of individual countries or other regions. Rates tend to be higher in more affluent countries, which may indicate the increased prevalence is due to increased rates of diagnosis. Although ulcerative colitis has no known cause, there is a presumed genetic component to susceptibility. The disease may be triggered in a susceptible person by environmental factors. Although dietary modification may reduce the discomfort of a person with the disease, ulcerative colitis is not thought to be caused by dietary factors. Ulcerative colitis is treated as an autoimmune disease. Treatment is with anti-inflammatory drugs, immunosuppression, and biological therapy targeting specific components of the immune response. Colectomy (partial or total removal of the large bowel through surgery) is occasionally necessary if the disease is severe, doesn't respond to treatment, or if significant complications develop. A total proctocolectomy (removal of the entirety of the large bowel) can be curative, but it may be associated with complications.

Metabolic syndrome is a combination of medical disorders that, when occurring together, increase the risk of developing cardiovascular disease and diabetes. Some studies have shown the prevalence in the USA to be an estimated 25% of the population, and prevalence increases with age. Metabolic syndrome is also known as metabolic syndrome X, cardiometabolic syndrome, syndrome X, insulin resistance syndrome, Reaven's syndrome (named for Gerald Reaven), and CHAOS (in Australia). The exact mechanisms of the complex pathways of metabolic syndrome are not yet completely known. The pathophysiology is extremely complex and has been only partially elucidated. Most patients are older, obese, sedentary, and have a degree of insulin resistance. Stress can also be a contributing factor. The most important factors are weight, genetics, endocrine disorders (such as polycystic ovary syndrome in women of reproductive age), aging, and sedentary lifestyle, (i.e., low physical activity and excess caloric intake). There is debate regarding whether obesity or insulin resistance is the cause of the metabolic syndrome or if they are consequences of a more far-reaching metabolic derangement. A number of markers of systemic inflammation, including C-reactive protein, are often increased, as are fibrinogen, interleukin 6, tumor necrosis factor-alpha (TNFα), and others. Some have pointed to a variety of causes, including increased uric acid levels caused by dietary fructose. Central obesity is a key feature of the syndrome, reflecting the fact that the syndrome's prevalence is driven by the strong relationship between waist circumference and increasing adiposity. However, despite the importance of obesity, patients who are of normal weight may also be insulin-resistant and have the syndrome. An estimated 75% of British patients with type 2 diabetes or impaired glucose tolerance (IGT) have metabolic syndrome. The presence of metabolic syndrome in these populations is associated with a higher prevalence of CVD than found in patients with type 2 diabetes or IGT without the syndrome.

Hypoadiponectinemia has been shown to increase insulin resistance, and is considered to be a risk factor for developing metabolic syndrome. The approximate prevalence of the metabolic syndrome in patients with coronary heart disease (CHD) is 50%, with a prevalence of 37% in patients with premature coronary artery disease (age 45), particularly in women. With appropriate cardiac rehabilitation and changes in lifestyle (e.g., nutrition, physical activity, weight reduction, and, in some cases, drugs), the prevalence of the syndrome can be reduced. Lipodystrophic disorders in general are associated with metabolic syndrome. Both genetic (e.g., Berardinelli-Seip congenital lipodystrophy, Dunnigan familial partial lipodystrophy) and acquired (e.g., HIV-related lipodystrophy in patients treated with highly active antiretroviral therapy) forms of lipodystrophy may give rise to severe insulin resistance and many of metabolic syndrome's components.

For many of these autoimmune disease there is no cure yet. It would be beneficial if the risk of autoimmune disease is reduced, or to treat or ameliorate the symptoms of autoimmune disease.

It has been surprisingly found that peptides selected from a casein hydrolysate reduces the risk of autoimmune diseases.

BRIEF SUMMARY

In a first aspect, the present disclosure is directed to a method for reducing the risk of autoimmune disease by administering a composition comprising peptides selected from a casein hydrolysate.

In a second aspect, the present disclosure is directed to a method to treat autoimmune disease by administering a composition comprising peptides selected from a casein hydrolysate.

In a further aspect, the present disclosure is directed to a method to reduce the symptoms of autoimmune disease by administering a composition comprising peptides selected from a casein hydrolysate.

In a preferred embodiment of the disclosure and/or embodiments thereof the autoimmune disease is selected from the group consisting of type 1 diabetes, Crohn's disease, Ulcerative colitis, Metabolic syndrome, HLA-DQ8 related diseases, HLA-DQ2 related diseases, and Coeliac disease.

In a preferred embodiment of the disclosure and/or embodiments thereof the composition comprising peptides selected from a casein hydrolysate is a nutritional composition.

In a preferred embodiment of the disclosure and/or embodiments thereof the casein hydrolysate is a cow's milk hydrolysate.

In a preferred embodiment of the disclosure and/or embodiments thereof the hydrolysate is an extensively hydrolyzed cow's milk peptide-containing hydrolysate.

In a preferred embodiment of the disclosure and/or embodiments thereof the hydrolysate consists of peptides with a molecular weight of more than 500 Da.

In a preferred embodiment of the disclosure and/or embodiments thereof the hydrolysate comprises at least one peptide selected from the group consisting of SEQ ID NO:

1-68, preferably at least 2 peptides, preferably at least 3 peptides, preferably at least 4 peptides, preferably at least 5 peptides.

In a preferred embodiment of the disclosure and/or embodiments thereof the hydrolysate comprises at least one peptide selected from the group consisting of SEQ ID NO: 1-24, preferably at least 2 peptides, preferably at least 3 peptides, preferably at least 4 peptides, preferably at least 5 peptides.

In a preferred embodiment of the disclosure and/or embodiments thereof the hydrolysate comprises at least one peptide selected from the group consisting of SEQ ID NO: 1-15, preferably at least 2 peptides, preferably at least 3 peptides, preferably at least 4 peptides, preferably at least 5 peptides.

In a preferred embodiment of the disclosure and/or embodiments thereof the hydrolysate comprises at least one peptide selected from the group consisting of SEQ ID NO: 1-12, preferably at least 2 peptides, preferably at least 3 peptides, preferably at least 4 peptides, preferably at least 5 peptides.

In a preferred embodiment of the disclosure and/or embodiments thereof the hydrolysate is administered in a nutritional composition, comprising a lipid or a fat phase, and a protein source.

In a preferred embodiment of the disclosure and/or embodiments thereof the nutritional composition comprises about 0.1 to about 1 g/100 kcal of a prebiotic composition, wherein the prebiotic composition comprises at least 20% of an oligosaccharide.

In a preferred embodiment of the disclosure and/or embodiments thereof the nutritional composition further comprises about 5 to about 100 mg/100 kcal of a source of long chain polyunsaturated fatty acids which comprises docosahexanoic acid.

In a preferred embodiment of the disclosure and/or embodiments thereof the nutritional composition further comprises arachidonic acid.

In a preferred embodiment of the disclosure and/or embodiments thereof hydrolysate is administered to a human, preferably a child or juvenile.

In a preferred embodiment of the disclosure and/or embodiments thereof hydrolysate is administered to an adult.

In a preferred embodiment of the disclosure and/or embodiments thereof the human has a cow's milk allergy.

DETAILED DESCRIPTION

Figure 1:
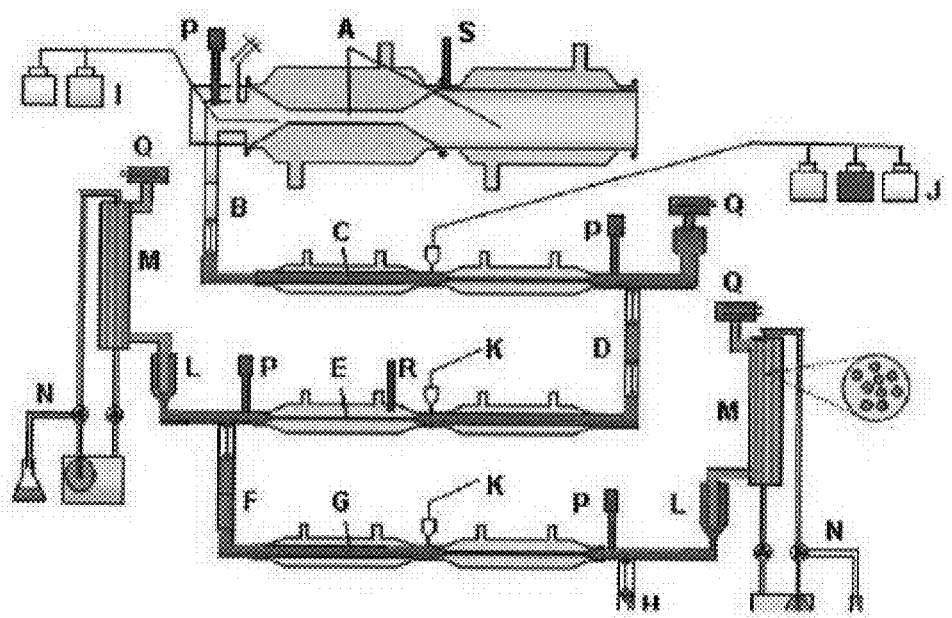
FIG. 1: Schematic figure of the TIM-1 model: A. stomach compartment; B. pyloric sphincter; C duodenum compartment; D peristaltic valve; E. jejunum compartment; F. peristaltic valve; G. ileum compartment; H. ileo-caecal sphincter; l. stomach secretion; J. duodenum secretion; K jejunum/ileum secretion; L. pre-filter; M. semi permeable membrane; N. water absorption; p pH electrodes; e. level sensors; R temperature sensor; S pressure sensor.

The term "nutritional composition" as used herein describes a solid or liquid formulation which can therefore be eaten or drunk by a human subject for nutrition. The nutritional composition of the disclosure preferably has a nutritional value of at least 1, more preferred at least 10 and even more preferred 50 kcal (kilo calorie)/100 ml for liquid formulations and preferably at least 1, more preferred at least 10, even more preferred at least 50, such as at least 100, and most preferred at least 300 kcal/100 g for dry food formulations. In a preferred embodiment of the disclosure the nutritional formulation of the disclosure has a nutritional value of at least 50-200 kcal/100 ml for liquid formulations and at least 300-600 kcal/100 g for dry food formulations. A nutritional composition is distinguished from a vaccine. In contrast to a vaccine, a nutritional composition does not comprise any of adjuvants (unless as contaminations), activated or inactivated viral compounds (unless as contaminations), activated or inactivated bacterial compounds (unless as contaminations), and pathogenic compounds (unless as contaminations). The term "supplement" as used herein relates to a nutritional supplement which is a concentrated source of nutrient or alternatively other substances with a nutritional or physiological effect whose purpose is to supplement the normal diet.

In addition to the above recited ingredients further ingredients may be selected from lipids, minerals, carbohydrates, amino acids, amino acid chelates, anabolic nutrients, vitamins, antioxidants, probiotic bacterial strain and lipotropic agents in order to provide an optimal sustained energy and anabolic nutritional formulation. The nutritional composition may be a nutritional supplement or may provide complete nutrition. Preferably the nutritional composition is in the form of a dry food concentrate. The nutritional composition of the disclosure provides a human subject with increasing preference with at least 5%, at least 10%, at least 25%, at least 50%, at least 75% or at least 90% of the daily calorie requirement of a human subject. The person skilled in the art is well aware that the daily calorie requirement is dependent on the gender, height and age of a human subject. For example, a 30 year old male of 80 kg body weight and 180 cm height has a daily calorie requirement of around 2900 cal (calories) to maintain his body weight whereas a 30 year old female of 55 kg body weight and 165 cm height has a daily calorie requirement of around 2100 cal to maintain her body weight. In a preferred embodiment, the nutritional formulation of the present disclosure is an infant or a nutritional product for infants or juvenile.

The term "peptide" as used herein describes linear molecular chains of amino acids, including single chain molecules or their fragments. A peptide in accordance with the disclosure contains with increasing preference about 2 to 100 amino acids, about 5 to 50 amino acids, or about 5 to 40 amino acids. Peptides may further form oligomers consisting of at least two identical or different molecules. The corresponding higher order structures of such multimers are, correspondingly, termed homo- or heterodimers, homo- or heterotrimers etc. Furthermore, peptidomimetics of such peptides where amino acid(s) and/or peptide bond(s) have been replaced by functional analogs are also encompassed by the term "peptide". Such functional analogues include all known amino acids other than the 20 gene-encoded amino acids, such as selenocysteine. The term "peptide" also refers to naturally modified peptides where the modification is effected e.g. by glycosylation, acetylation, phosphorylation and similar modifications which are well known in the art. A peptide has to be distinguished from a protein in the present disclosure. A protein in accordance with the present disclosure describes an organic compound made of amino acids arranged in a linear chain and folded into a globular form. Furthermore, a protein in accordance with the present disclosure describes a chain of amino acids of more than 100 amino acids. Peptides may, e.g., be produced recombinantly, (semi-) synthetically, or obtained from natural sources such as after hydrolysation of proteins, all according to methods known in the art.

The term "casein hydrolysate" as used herein defines a formula which comprises peptides derived from hydrolyzed cow's casein milk proteins. In this regard, a hydrolyzed protein is a protein that has been broken down into peptides and/or component amino acids. While there are many means of achieving protein hydrolysis, two of the most common means are prolonged boiling in a strong acid or strong base or using an enzyme such as the pancreatic protease enzyme to stimulate the naturally-occurring hydrolytic process. Hydrolysis of proteins derived from milk is preferably achieved using an enzyme or a mixture of enzyme. A casein cow milk hydrolysate can comprise peptides derived from milk, wherein the proteins of said milk have been hydrolyzed to various degrees. Accordingly, one can distinguish between a partially hydrolyzed cow's milk peptide-containing hydrolysate and an extensively hydrolyzed cow's milk peptide-containing hydrolysate. In this regard, a partially hydrolyzed cow's milk peptide-containing hydrolysate comprises more than 20% of intact cow's milk protein whereas an extensively hydrolyzed cow's milk peptide-containing hydrolysate comprises less than 1% of peptides having a size of greater than 1.5 kD. Furthermore, an extensively hydrolyzed cow's milk peptide-containing hydrolysate is preferably hypoallergenic.

The term "peptide derived from cow's milk" as used herein defines a peptide which has an amino acid sequence which is a partial amino acid sequence of a cow's milk protein. Such peptides may be obtained as outlined above by hydrolysis or may be synthesized in vitro by methods known to the skilled person and described in the examples of the disclosure.

The term "peptide-containing fraction of the hydrolysate" refers to a mixture of peptides comprising at least 2, preferably at least 5, more preferably at least 10 and most preferably at least 20 which have been isolated from the hydrolysate of the disclosure by filtration techniques which are known to the skilled person. Furthermore, techniques for the isolation of peptides from the hydrolysate of the disclosure are described herein below.

The term "child" or the term "juvenile" is used herein in accordance with the definitions provided in the art. Thus, the term "child" means a human subject between the stages of birth and the age of about 10 and the term "juvenile" means a human subject between the age of about 10 and puberty (before sexual maturity).

The term "adult" is used herein in accordance with the definitions provided in the art. Thus, this term means a human subject after puberty (after sexual maturity). A further preferred embodiment of the disclosure relates to the nutritional formulation of the disclosure, wherein the human subject has a cow's milk allergy.

The term "cow's milk allergy" describes a food allergy, i.e. an immune adverse reaction to one or more of the proteins contained in cow's milk in a human subject. The principal symptoms are gastrointestinal, dermatological and respiratory symptoms. These can translate into skin rashes, hives, vomiting, diarrhea, constipation and distress. The clinical spectrum extends to diverse disorders: anaphylactic reactions, atopic dermatitis, wheeze, infantile colic, gastro esophageal reflux disease (GERD), esophagitis, colitis gastroenteritis, headache/migraine and constipation.

In a preferred embodiment of the disclosure and/or embodiments thereof the autoimmune disease is selected from the group consisting of type 1 diabetes, Crohn's disease, Ulcerative colitis, Metabolic syndrome, HLA-DQ8 related diseases, HLA-DQ2 related diseases, Celiac disease. More preferably, the autoimmune disease is selected from the group consisting of type 1 diabetes, Metabolic syndrome, HLA-DQ8 related diseases, HLA-DQ2 related diseases. Even more preferably the autoimmune disease is selected from the group consisting of type 1 diabetes, HLA-DQ8 related diseases, and HLA-DQ2 related diseases. More preferably the autoimmune disease is type 1 diabetes.

The present inventors have surprisingly found that peptides selected from a casein hydrolysate has a beneficial effect on the risk factors of autoimmune disease and especially type 1 diabetes.

It was also found that an extensively hydrolyzed cow's milk peptide-containing hydrolysate had positive effects on the on the risk factors of autoimmune disease and especially type 1 diabetes. Suitable hydrolysates include casein hydrolysates. It was furthermore found that dialysis of the hydrolysate with a cut-off of 500 Da so as to include peptide sequences 500 Da and larger renders a hydrolysate fraction that has even better effect on the risk factors of autoimmune disease and especially type 1 diabetes. Accordingly, in particular embodiments, the hydrolysate comprises peptides with a molecular weight of more than 500 Da, and in further embodiments, the hydrolysate comprises peptides with a molecular weight in a range of 500 to 2000 Da. In other embodiments, the hydrolysate consists of peptides with a molecular weight of more than 500 Da, and in further embodiments, the hydrolysate consists of peptides with a molecular weight in a range of 500 to 2000 Da.

The following peptides have been identified as possibly contributing the beneficial effect on the autoimmune response and/or type 1 diabetes:

TABLE 1

| identified peptide in the hydrolysate: | |
|---|---|
| SEQ ID NO: 1* | IPNPIG |
| SEQ ID NO: 2 | IGSESTEDQ |
| SEQ ID NO 3: | DKTEIPT |
| SEQ ID NO: 4 | IVPN |
| SEQ ID NO: 5 | LEDSPE |
| SEQ ID NO: 6 | NQEQPI |
| SEQ ID NO: 7 | NVPGE |
| SEQ ID NO: 8 | PFPGPI |
| SEQ ID NO: 9 | TEDEL |
| SEQ ID NO: 10 | VPSE |
| SEQ ID NO: 11 | YPFPGP |
| SEQ ID NO: 12 | YPSGA |
| SEQ ID NO 13 | FPGPIP |
| SEQ ID NO: 14 | MHQPHQPLPPT |
| SEQ ID NO: 15 | YPFPGPIPN |
| SEQ ID NO: 16 | DMEST |
| SEQ ID NO: 17 | FPGPIPN |
| SEQ ID NO: 18 | IPNPI |
| SEQ ID NO: 19 | MESTEV |
| SEQ ID NO: 20 | PGPIPN |
| SEQ ID NO: 21 | PHQPLPPT |
| SEQ ID NO: 22 | PNPI |
| SEQ ID NO: 23 | SKDIGSE |
| SEQ ID NO: 24 | YPFPGPIP |
| SEQ ID NO: 25 | AINPSKEN |
| SEQ ID NO: 26 | APFPE |
| SEQ ID NO: 27 | DIGSES |
| SEQ ID NO: 28 | DMPI |
| SEQ ID NO: 29 | DVPS |
| SEQ ID NO: 30 | EDI |
| SEQ ID NO: 31 | ELF |
| SEQ ID NO: 32 | EMP |
| SEQ ID NO: 33 | ETAPVPL |
| SEQ ID NO: 34 | GPFP |
| SEQ ID NO: 35 | GPIV |
| SEQ ID NO: 36 | IGSSSEES |
| SEQ ID NO: 37 | IGSSSEESA |
| SEQ ID NO: 38 | INPSKE |
| SEQ ID NO: 39 | IPPLTQTPV |
| SEQ ID NO: 40 | ITAP |
| SEQ ID NO: 41 | KHQGLPQ |
| SEQ ID NO: 42 | LDVTP |
| SEQ ID NO: 43 | LPLPL |

TABLE 1-continued

| identified peptide in the hydrolysate: | |
|---|---|
| SEQ ID NO: 44 | NAVPI |
| SEQ ID NO: 45 | NEVEA |
| SEQ ID NO: 46 | NLL |
| SEQ ID NO: 47 | PITPT |
| SEQ ID NO: 48 | PNSLPQ |
| SEQ ID NO: 49 | PQLEIVPN |
| SEQ ID NO: 50 | PQNIPPL |
| SEQ ID NO: 51 | PVLGPV |
| SEQ ID NO: 52 | PVPQ |
| SEQ ID NO: 53 | PVVVP |
| SEQ ID NO: 54 | PVVVPP |
| SEQ ID NO: 55 | SIGSSSEESAE |
| SEQ ID NO: 56 | SISSSEE |
| SEQ ID NO: 57 | SISSSEEIVPN |
| SEQ ID NO: 58 | SPPEIN |
| SEQ ID NO: 59 | SPPEINT |
| SEQ ID NO: 60 | TDAPSFS |
| SEQ ID NO: 61 | VATEEV |
| SEQ ID NO: 62 | VLPVP |
| SEQ ID NO: 63 | VPGE |
| SEQ ID NO: 64 | VPGEIV |
| SEQ ID NO: 65 | VPITPT |
| SEQ ID NO: 66 | VVPPFLQPE |
| SEQ ID NO: 67 | VVVPP |
| SEQ ID NO: 68 | YPVEP |

In a preferred embodiment of the present disclosure and/or embodiments thereof the hydrolysate comprises a peptide with SEQ ID NO: 1 and at least one peptide selected from the group consisting of SEQ ID NO: 2-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO:1, and SEQ ID NO: 3-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO:1-2, and SEQ ID NO: 4-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO:1-3, and SEQ ID NO: 5-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO:1-4, and SEQ ID NO: 6-68, preferably at least 2 peptides, preferably at least 3 peptides, preferably at least 4 peptides, preferably at least 5 peptides.

In a preferred embodiment of the present invention and/or embodiments thereof the hydrolysate comprises a peptide with SEQ ID NO: 6 and at least one peptide selected from the group consisting of SEQ ID NO:1-5, and SEQ ID NO: 7-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO:1-6, and SEQ ID NO: 8-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO:1-7, and SEQ ID NO: 9-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO:1-8, and SEQ ID NO: 10-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO:1-9, and SEQ ID NO: 11-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO:1-10, and SEQ ID NO: 12-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO:1-11, and SEQ ID NO: 13-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO:1-12, and SEQ ID NO: 14-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO:1-13, and SEQ ID NO: 15-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO:1-14, and SEQ ID NO: 16-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO:1-15, and SEQ ID NO: 17-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO:1-16, and SEQ ID NO: 18-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO:1-17, and SEQ ID NO: 19-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO:1-18, and SEQ ID NO: 20-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO:1-19, and SEQ ID NO: 21-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO:1-20, and SEQ ID NO: 22-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO:1-21, and SEQ ID NO: 23-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO:1-22, and SEQ ID NO: 24-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO:1-23, and SEQ ID NO: 25-68, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 1 and at least one peptide selected from the group consisting of SEQ ID NO: 2-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO:1, and SEQ ID NO: 3-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO:1-2, and SEQ ID NO: 4-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO:1-3, and SEQ ID NO: 5-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO:1-4, and SEQ ID NO: 6-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO:1-5, and SEQ ID NO: 7-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO:1-6, and SEQ ID NO: 8-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO:1-7, and SEQ ID NO: 9-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO:1-8, and SEQ ID NO: 10-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO:1-9, and SEQ ID NO: 11-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO:1-10, and SEQ ID NO: 12-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO:1-11, and SEQ ID NO: 13-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO:1-12, and SEQ ID NO: 14-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO:1-13, and SEQ ID NO: 15-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO:1-14, and SEQ ID NO: 16-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO:1-15, and SEQ ID NO: 17-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO:1-16, and SEQ ID NO: 18-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO:1-17, and SEQ ID NO: 19-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO:1-18, and SEQ ID NO: 20-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO:1-19, and SEQ ID NO: 21-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO:1-20, and SEQ ID NO: 22-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO:1-21, and SEQ ID NO: 23-24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO:1-22, and SEQ ID NO: 24, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO:1-23, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 1 and at least one peptide selected from the group consisting of SEQ ID NO: 2-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO:1, and SEQ ID NO: 3-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO:1-2, and SEQ ID NO: 4-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO:1-3, and SEQ ID NO: 5-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO:1-4, and SEQ ID NO: 6-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO:1-5, and SEQ ID NO: 7-15, preferably at least 2 peptides, preferably at least 3 peptides, preferably at least 4 peptides, preferably at least 5 peptides.

Ina preferred embodiment of the present disclosure and/or embodiments thereof the hydrolysate comprises a peptide with SEQ ID NO: 7 and at least one peptide selected from the group consisting of SEQ ID NO:1-6, and SEQ ID NO: 8-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO:1-7, and SEQ ID NO: 9-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO:1-8, and SEQ ID NO: 10-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO:1-9, and SEQ ID NO: 11-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO:1-10, and SEQ ID NO: 12-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO:1-11, and SEQ ID NO: 13-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO:1-12, and SEQ ID NO: 14-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO:1-13, and SEQ ID NO: 15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO:1-14, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO:1-15, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 1 and at least one peptide selected from the group consisting of SEQ ID NO: 2-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 2 and at least one peptide selected from the group consisting of SEQ ID NO:1, and SEQ ID NO: 3-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 3 and at least one peptide selected from the group consisting of SEQ ID NO:1-2, and SEQ ID NO: 4-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 4 and at least one peptide selected from the group consisting of SEQ ID NO:1-3, and SEQ ID NO: 5-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 5 and at least one peptide selected from the group consisting of SEQ ID NO:1-4, and SEQ ID NO: 6-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 6 and at least one peptide selected from the group consisting of SEQ ID NO:1-5, and SEQ ID NO: 7-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 7 and at least one peptide selected from the group consisting of SEQ ID NO:1-6, and SEQ ID NO: 8-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 8 and at least one peptide selected from the group consisting of SEQ ID NO:1-7, and SEQ ID NO: 9-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 9 and at least one peptide selected from the group consisting of SEQ ID NO:1-8, and SEQ ID NO: 10-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 10 and at least one peptide selected from the group consisting of SEQ ID NO:1-9, and SEQ ID NO: 11-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 11 and at least one peptide selected from the group consisting of SEQ ID NO:1-10, and SEQ ID NO: 12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 12 and at least one peptide selected from the group consisting of SEQ ID NO:1-11, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 13 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 14 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 15 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 16 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 17 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 18 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 19 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 20 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 21 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 22 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 23 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate comprises a peptide with SEQ ID NO: 24 and at least one peptide selected from the group consisting of SEQ ID NO:1-12, preferably at least 2 peptides, preferably at least 3 peptides, preferably at least 4 peptides, preferably at least 5 peptides.

In a preferred embodiment of the present disclosure and/or embodiments thereof the hydrolysate is a hydrolysate comprising combinations of SEQ ID NO: 1, and SEQ ID NO: 2.

In a preferred embodiment of the present disclosure and/or embodiments thereof the hydrolysate is a hydrolysate comprising combinations of SEQ ID NO: 1, and SEQ ID NO: 3.

In a preferred embodiment of the present disclosure and/or embodiments thereof the hydrolysate is a hydrolysate comprising combinations of SEQ ID NO: 1, and SEQ ID NO: 4.

In a preferred embodiment of the present disclosure and/or embodiments thereof the hydrolysate is a hydrolysate comprising combinations of SEQ ID NO: 1, and SEQ ID NO: 5.

In a preferred embodiment of the present disclosure and/or embodiments thereof the hydrolysate is a hydrolysate comprising combinations of SEQ ID NO: 1, and SEQ ID NO: 6.

In a preferred embodiment of the present disclosure and/or embodiments thereof the hydrolysate is a hydrolysate comprising combinations of SEQ ID NO: 1, and SEQ ID NO: 7.

In a preferred embodiment of the present disclosure and/or embodiments thereof the hydrolysate is a hydrolysate comprising combinations of SEQ ID NO: 1, and SEQ ID NO: 8.

In a preferred embodiment of the present disclosure and/or embodiments thereof the hydrolysate is a hydrolysate comprising combinations of SEQ ID NO: 1, and SEQ ID NO: 9.

In a preferred embodiment of the present disclosure and/or embodiments thereof the hydrolysate is a hydrolysate comprising combinations of SEQ ID NO: 1, and SEQ ID NO: 10.

In a preferred embodiment of the present disclosure and/or embodiments thereof the hydrolysate is a hydrolysate comprising combinations of SEQ ID NO: 1, and SEQ ID NO: 11.

In a preferred embodiment of the present disclosure and/or embodiments thereof the hydrolysate is a hydrolysate comprising combinations of SEQ ID NO: 1, and SEQ ID NO: 12.

In a preferred embodiment of the present disclosure and/or embodiments thereof the hydrolysate is a hydrolysate comprising combinations of SEQ ID NO: 1, and SEQ ID NO: 13.

In a preferred embodiment of the present disclosure and/or embodiments thereof the hydrolysate is a hydrolysate comprising combinations of SEQ ID NO: 1, and SEQ ID NO: 14.

In a preferred embodiment of the present disclosure and/or embodiments thereof the hydrolysate is a hydrolysate comprising combinations of SEQ ID NO: 1, and SEQ ID NO: 15.

In a preferred embodiment of the present disclosure and/or embodiments thereof the hydrolysate is a hydrolysate comprising combinations of SEQ ID NO: 1, and SEQ ID NO: 16.

In a preferred embodiment of the present disclosure and/or embodiments thereof the hydrolysate is a hydrolysate comprising combinations of SEQ ID NO: 1, and SEQ ID NO: 17.

In a preferred embodiment of the present disclosure and/or embodiments thereof the hydrolysate is a hydrolysate comprising combinations of SEQ ID NO: 1, and SEQ ID NO: 18.

In a preferred embodiment of the present disclosure and/or embodiments thereof the hydrolysate is a hydrolysate comprising combinations of SEQ ID NO: 1, and SEQ ID NO: 19.

In a preferred embodiment of the present disclosure and/or embodiments thereof the hydrolysate is a hydrolysate comprising combinations of SEQ ID NO: 1, and SEQ ID NO: 20.

In a preferred embodiment of the present disclosure and/or embodiments thereof the hydrolysate is a hydrolysate comprising combinations of SEQ ID NO: 1, and SEQ ID NO: 21.

In a preferred embodiment of the present disclosure and/or embodiments thereof the hydrolysate is a hydrolysate comprising combinations of SEQ ID NO: 1, and SEQ ID NO: 22.

In a preferred embodiment of the present disclosure and/or embodiments thereof the hydrolysate is a hydrolysate comprising combinations of SEQ ID NO: 1, and SEQ ID NO: 23.

In a preferred embodiment of the present disclosure and/or embodiments thereof the hydrolysate is a hydrolysate comprising combinations of SEQ ID NO: 1, and SEQ ID NO: 24.

In a preferred embodiment of the disclosure and/or embodiments thereof the nutritional formulation additionally comprises one or more of carbohydrates, nucleic acids, lipids, minerals, anabolic nutrients, vitamins, antioxidants, probiotic bacterial strains and lipotropic agents.

In a preferred embodiment of the present disclosure and/or embodiments thereof the nutritional composition comprises a fat phase wherein the lipid or fat is present at a level of up to about 7 g/100 kcal.

In a preferred embodiment of the present disclosure and/or embodiments thereof the nutritional composition wherein the protein source is present at a level of up to about 5 g/100 kcal.

In a preferred embodiment of the present disclosure and/or embodiments thereof the nutritional composition comprises an oligosaccharide wherein the oligosaccharide comprises galacto-oligosaccharide.

In a preferred embodiment of the present disclosure and/or embodiments thereof the nutritional composition further comprises polydextrose.

The present disclosure is also directed to a peptide-containing fraction of a casein hydrolysate for use in reducing the risk of autoimmune disease, treatment of autoimmune disease, and/or reducing the symptoms of autoimmune disease, wherein the autoimmune disease is type 1 diabetes in some embodiments.

The present disclosure is also directed to a composition comprising peptides selected from a casein hydrolysate for use in reducing the risk of autoimmune diseases by administering said composition, wherein the autoimmune disease is type 1 diabetes in some embodiments.

The present is also directed to a composition comprising peptides selected from a casein hydrolysate for use in treatment of autoimmune diseases by administering said composition, wherein the autoimmune disease is type 1 diabetes in some embodiments.

The present is also directed to a composition comprising peptides selected from a casein hydrolysate for use in reducing the symptoms of autoimmune disease by administering said composition, wherein the autoimmune disease is type 1 diabetes in some embodiments.

The present is also directed to peptides selected from a casein hydrolysate for use in use in reducing the risk of autoimmune disease, treatment of autoimmune disease, and/or reducing the symptoms of autoimmune disease, wherein the autoimmune disease is type 1 diabetes in some embodiments.

In a preferred embodiment of the present disclosure and/or embodiments thereof the composition comprising peptides selected from a casein hydrolysate is a nutritional composition.

In a preferred embodiment of the present disclosure and/or embodiments thereof the casein hydrolysate is a cow's milk hydrolysate.

In a preferred embodiment of the present disclosure and/or embodiments thereof the hydrolysate is an extensively hydrolyzed cow's milk peptide-containing hydrolysate.

The preferred embodiments of the method of the invention and/or embodiments thereof are also preferred embodiments of the casein hydrolysate for use reducing the risk of autoimmune disease, for use in treatment of autoimmune disease, and/or for use in reducing the symptoms of autoimmune disease.

The disclosure is now exemplified by the following non limiting examples.

EXAMPLES

Example 1

Digestion Model Set Up

All formulations (finished formulas and hydrolysates) were investigated in the TIM-1 system (TNO, Zeist, The Netherlands) simulating the average conditions in the stomach and small intestine of young children (0-0.5 year of age). These conditions included especially the dynamics of gastric emptying, the gastric and the intestinal pH values and the compositions and activities of the oral, gastric and intestinal secretion fluids such as electrolytes, digestive enzymes and bile. Digested and dialysed (to remove mono- and di-saccharides) materials of the finished products as well as undigested and digested and dialysed materials of the hydrolysates were used for infant fecal fermentation experiments to study possible effects on protein/peptide digestion by the colonic microbial community and to study the effects of these components on gut microbiota composition and metabolism. From the fecal fermentations, samples were taken at different time points and were subjected to different types of analyses.

FIG. 1 shows the setup. It shows a schematic figure of the TIM-1 model: A. stomach compartment; B. pyloric sphincter; C duodenum compartment; D peristaltic valve; E. jejunum compartment; F. peristaltic valve; G. ileum compartment; H. ileo-caecal sphincter; I. stomach secretion; J. duodenum secretion; K jejunum/ileum secretion; L. pre-filter; M. semi permeable membrane; N. water absorption; p pH electrodes; e. level sensors; R temperature sensor; S pressure sensor.

Figure 2:
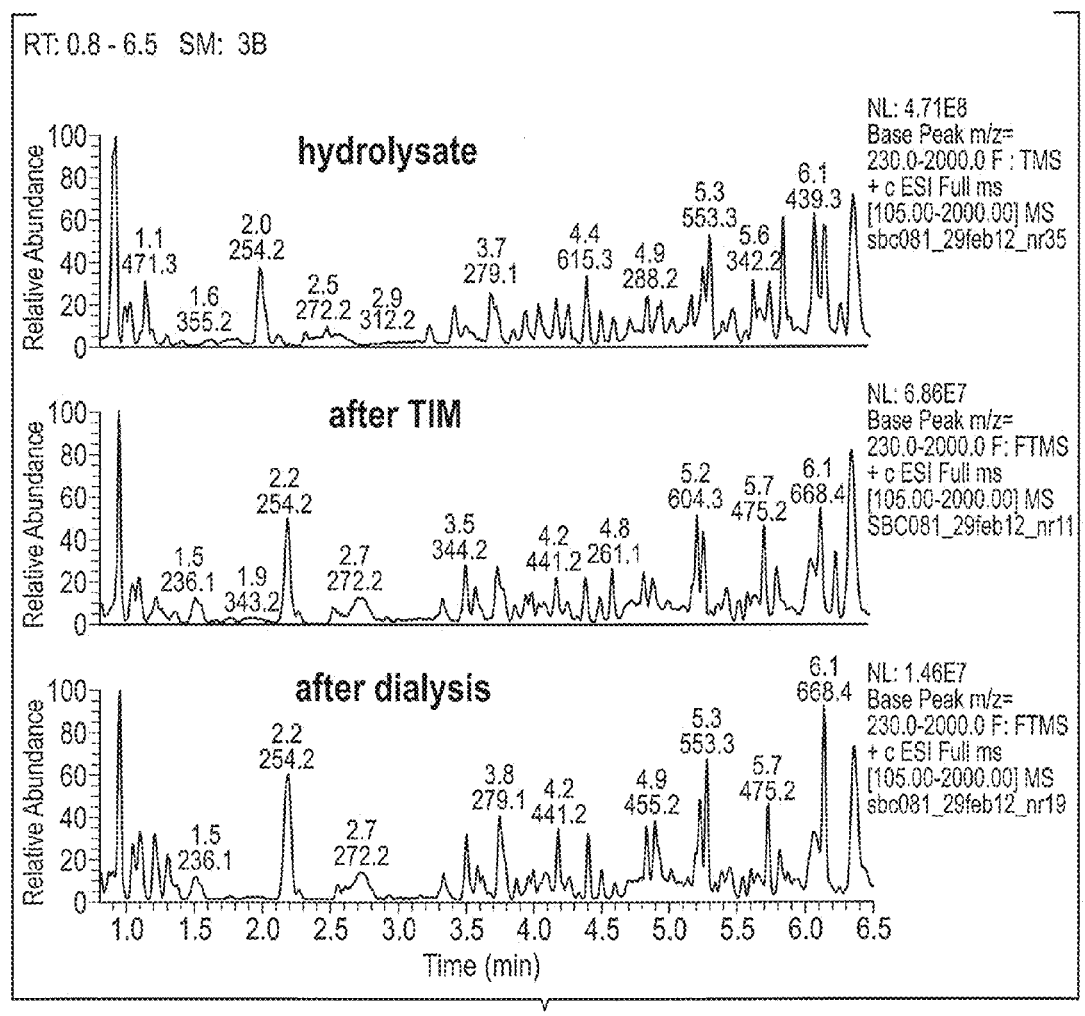
FIG. 2 Comparison of peptide profiles after simulated infant stomach digestion observed for a casein hydrolysate of the present disclosure by LC-MS (m/z 230-2000). Peptide profiling is depicted before digestion, after digestion (TIM), and after digestion and further dialysis.

Peptide Profiles after Stomach Digestion:

FIG. 2 shows a comparison of peptide profiles after simulated infant stomach digestion observed for the a casein hydrolysate of the present disclosure by LC-MS (mlz 230-2000). Peptide profiling is depicted before digestion, after digestion (TIM), and after digestion and further dialysis. The figures show that the peptide profile of the hydrolysate hardly changed during simulated stomach digestion.

Microbiota Composition and Metabolism

Figure 3:
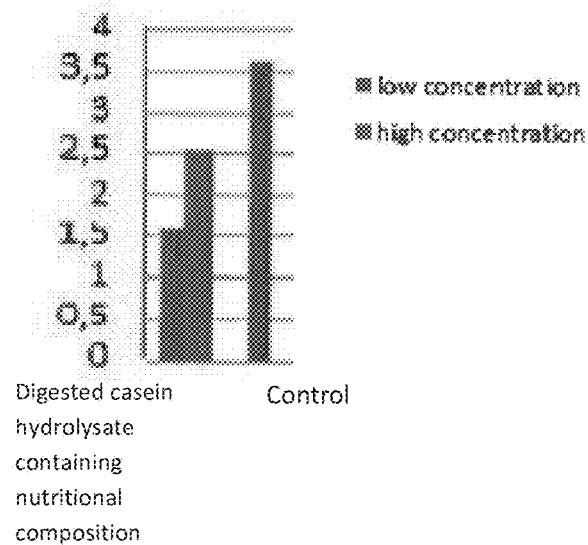
FIG. 3. Effect of a casein hydrolysate-containing nutritional composition of the present disclosure on *Bacteroides* genus level in the microbial community of the fecal fermentation experiment at T=18 following exposure to a digested casein hydrolysate-containing nutritional composition of the present disclosure (thus >500 Da) added at low (9.5 mg/ml) or high concentration (19 mg/ml) and determined with 454 pyrosequencing. The y-axis depicts the 10-log value of the number of sequences, which directly correlates to abundance.
Figure 4:
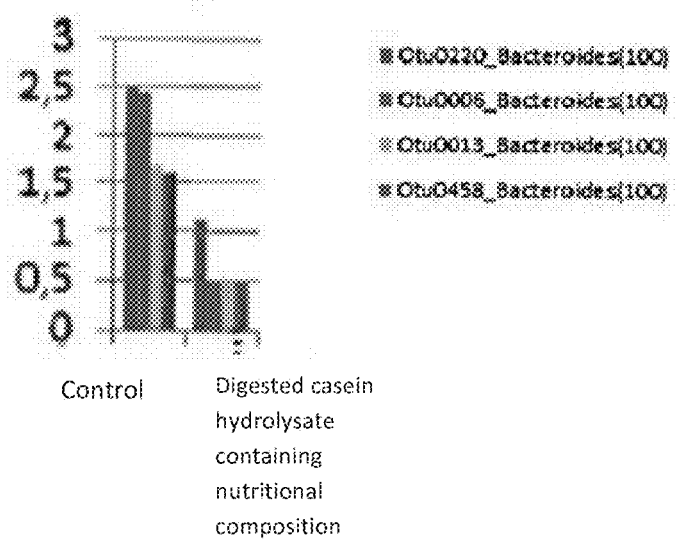
FIG. 4. Abundance of *Bacteroides* phylotypes in the microbial community of the fecal fermentation experiment at T=18 following exposure to a digested casein hydrolysate-containing nutritional composition of the present disclosure (thus >500 Da) added at low concentration and determined with 454 pyrosequencing. The four main *Bacteroides* species-like phylotypes (OTU's) are shown. The y-axis depicts the 10-log value of the number of sequences, which directly correlates to abundance.
Figure 5:
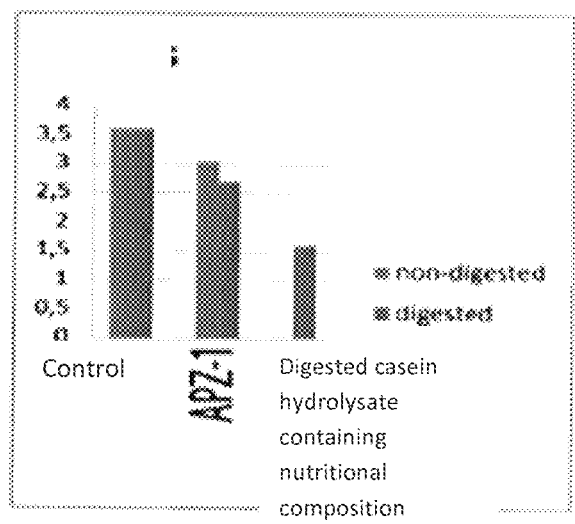
FIG. 5. Effect of a casein hydrolysate of the present disclosure (APZ-1) on *Bacteroides* genus level in the microbial community of the fecal fermentation experiment at T=18 following exposure to non-digested or digested (thus >500 Da) casein hydrolysate of the present disclosure added at low concentration and determined with 454 pyrosequencing. The y-axis depicts the 10-log value of the number of sequences correlating to abundance. The casein hydrolysate inhibited *Bacteroides* abundance, indicating that the effect of the finished product is partly mediated by the hydrolysate/peptide fraction present in the product. A casein hydrolysate-containing nutritional composition of the present disclosure (digested, at low concentration) is included as a reference.
Figure 6:
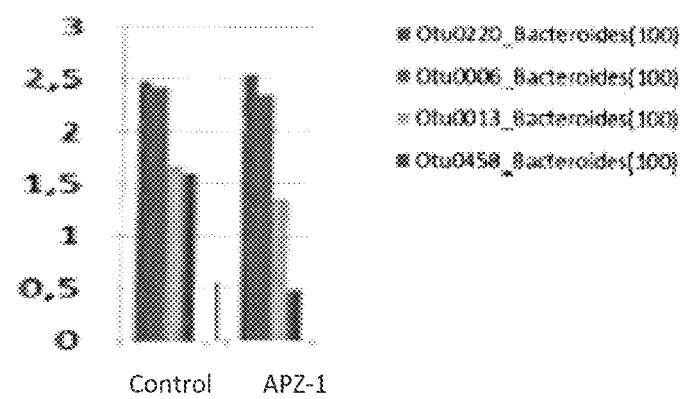
FIG. 6. Abundance of *Bacteroides* phylotypes in the microbial community of the fecal fermentation experiment at T=18 following exposure to digested (thus >500 Da) casein hydrolysate of the present disclosure (APZ-1) added at high concentration (19 mg/ml) and determined with 454 pyrosequencing. The y-axis depicts the 10-log value of the number of sequences, which directly correlates to abundance.
Figure 7:
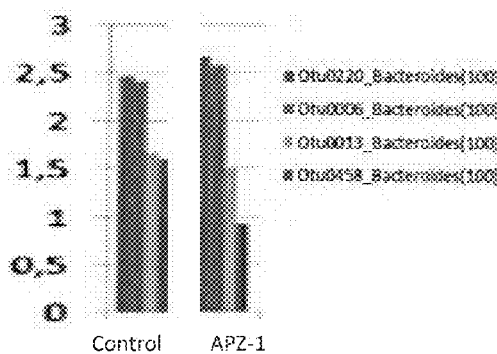
FIG. 7. Abundance of *Bacteroides* phylotypes in the microbial community of the fecal fermentation experiment at T=18 following exposure to digested (thus >500 Da) casein hydrolysate of the present disclosure (APZ-1) added at low concentration (9.5 mg/ml) and determined with 454 pyrosequencing. The y-axis depicts the 10-log value of the number of sequences, which directly correlates to abundance.

The below findings were generated with finished products or hydrolysates after dialyses, thus generating a product with peptides having a molecular weight of more than 500 Da. FIG. 3 shows the effect of a casein hydrolysate-containing nutritional composition of the present disclosure on *Bacteroides* genus level in the microbial community of the fecal fermentation experiment at T=18 following exposure to a digested casein hydrolysate-containing nutritional composition of the present disclosure (thus >500 Da) added at low or high concentration and determined with 454 pyrosequencing. The y-axis depicts the 10-log value of the number of sequences, which directly correlates to abundance. A casein hydrolysate-containing nutritional composition of the present disclosure clearly inhibited *Bacteroides* abundance, which may have been mediated by both carbohydrates as well as peptides present in the product. FIG. 4. Shows the abundance of *Bacteroides* phylotypes in the microbial community of the fecal fermentation experiment at T=18 following exposure to a digested casein hydrolysate-containing nutritional composition of the present disclosure (thus >500 Da) added at low concentration and determined with 454 pyrosequencing. The four main *Bacteroides* species-like phylotypes (OTU's) are shown. The y-axis depicts the 10-log value of the number of sequences, which directly correlates to abundance. The casein hydrolysate-containing nutritional composition clearly inhibited *Bacteroides* abundance, which may have been mediated by both carbohydrates as well as peptides present in the product. FIG. 5 shows the effect of a casein hydrolysate of the present disclosure (APZ-1) on *Bacteroides* genus level in the microbial community of the fecal fermentation experiment at T=18 following exposure to non-digested or a digested (thus >500 Da) casein hydrolysate of the present disclosure added at low concentration and determined with 454 pyrosequencing. The y-axis depicts the 10-log value of the number of sequences correlating to abundance. A casein hydrolysate of the present disclosure inhibited *Bacteroides* abundance, indicating that the effect of the finished product is partly mediated by the hydrolysate/peptide fraction present in the product. A casein hydrolysate-containing nutritional composition of the present disclosure (digested, at low concentration) is included as a reference. FIGS. 6 & 7 shows the abundance of *Bacteroides* phylotypes in the microbial community of the fecal fermentation experiment at T=18 following exposure to a digested (thus >500 Da) casein hydrolysate of the present disclosure (APZ-1) added at high (FIG. 6) (19 mg/ml) or low (FIG. 7) concentration (9.5 mg/ml) and determined with 454 pyrosequencing. The y-axis depicts the 10-log value of the number of sequences, which directly correlates to abundance. A casein hydrolysate of the present disclosure clearly inhibited *Bacteroides* abundance, indicating that the effect of the finished product is partly mediated by the hydrolysate/peptide fraction present in the product. Interestingly, the hydrolysate mainly affects OTU 013 and 458, related to *B. stercoris/uniformis*, whereas little to no effect was observed on OTUs 006 (*B. thetaiotaomicron* group) and 0220 (*B. fragilis* group). In literature (Giongo et al, 2010), increased abundance of *B. uniformis* has been observed in the microbiota of children developing T1D and *B. fragilis* in control children, implying that the effects of the hydrolysate on these groups may be beneficial against the development of T1D.

In the in vitro model of infant fecal sample fermentation there was no obvious effect of the casein hydrolysate-containing nutritional composition of the present disclosure or casein hydrolysate of the present disclosure on Bifidobacteria composition. The abundance of *Bacteroides* species was severely impacted following exposure of the faecal community to various commercial products including a casein hydrolysate-containing nutritional composition of the present disclosure, and this may also involve carbohydrate fermentation. Exposure of the faecal ecosystem to the hydrolysates impacted the *Bacteroides* group, as determined by qPCR. There was a significant growth inhibiting effect of a casein hydrolysate of the present disclosure on *Bacteroides stercoris/uniformis* group. There was little to no effect on *B. thetaiotamicron* or *B. fragilis* group. Note that certain *Bacteroides* species, *ovatus, fragilis, vulgates, uniformis* may have been associated with auto-immune or chronic inflammatory diseases. In this respect reduction of *Bacteroides* species could imply a potential health benefit.

Amino Acids and Short Chain Fatty Acids

Figure 8:
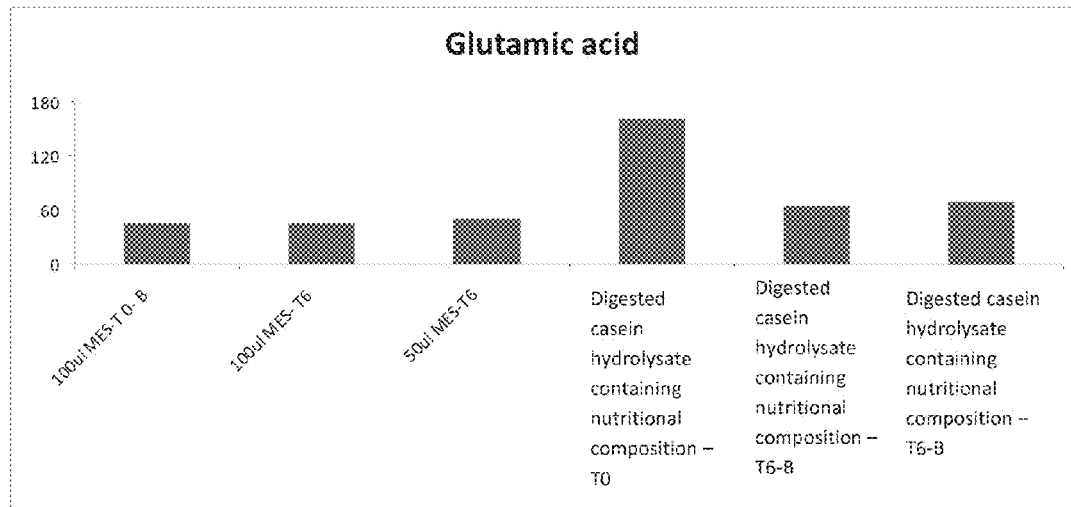
FIG. 8. Concentration (microgram/ml) of Glutamic acid at T=0 and T=6 of the fecal fermentation experiments with digested (thus >500 Da) casein hydrolysate-containing nutritional composition of the present disclosure finished product at low concentration. Control conditions with MES buffer.

FIG. 8 shows the concentration of Glutamic acid at T=0 and T=6 of the fecal fermentation experiments with a digested (thus >500 Da) casein hydrolysate-containing nutritional composition of the present disclosure at low concentration. Control conditions with MES buffer. Glutamate concentration (microgram/ml) as added with finished product decreased during fermentation. This could indicate a beneficial effect since elevated levels of glutamate in plasma are associated with T1D onset (Oresic et al, 2008).

Figure 9:
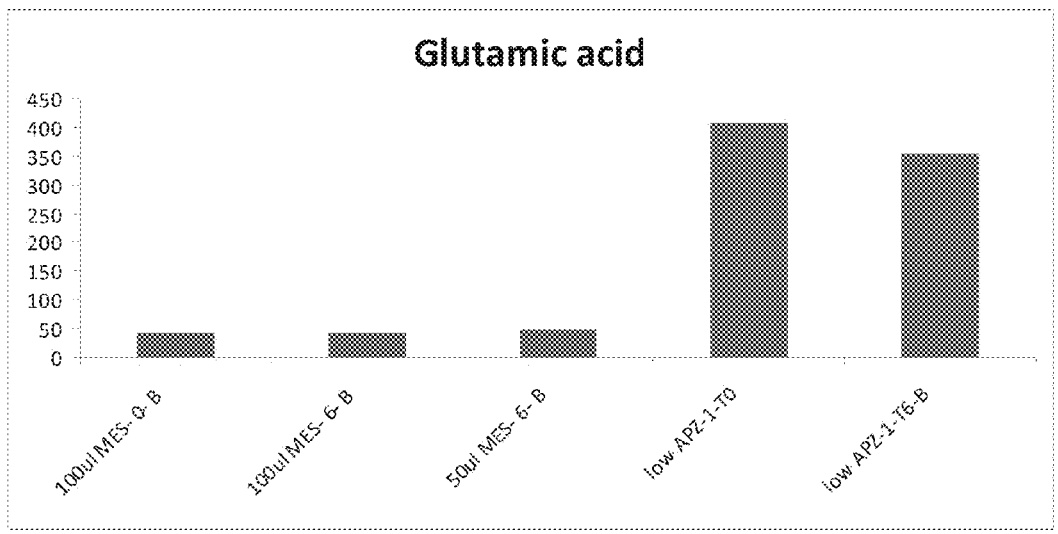
FIG. 9. Concentration (microgram/ml) of Glutamic acid at T=0 and T=6 of the fecal fermentation experiments with a non-digested casein hydrolysate of the present disclosure (APZ-1) added at low concentration. Control conditions with MES buffer.

FIG. 9 shows the concentration of Glutamic acid at T=0 and T=6 of the fecal fermentation experiments with a non-digested casein hydrolysate of the present disclosure (APZ-1) added at low concentration. Control conditions with MES buffer. The concentration (microgram/ml) of glutamate as added with the hydrolysate slightly decreased during the fermentation, indicating that the effects of a casein hydrolysate-containing nutritional composition of the present disclosure on glutamate levels might partly be mediated by the hydrolysate/peptide fraction present in the product.

Production of glutamate decreased after fermentation of a casein hydrolysate-containing nutritional composition of the present disclosure, a casein hydrolysate and amino acid containing nutritional composition of the present disclosure and Similac, accompanied by increased proline and threonine as compared to other products.

Figure 10:
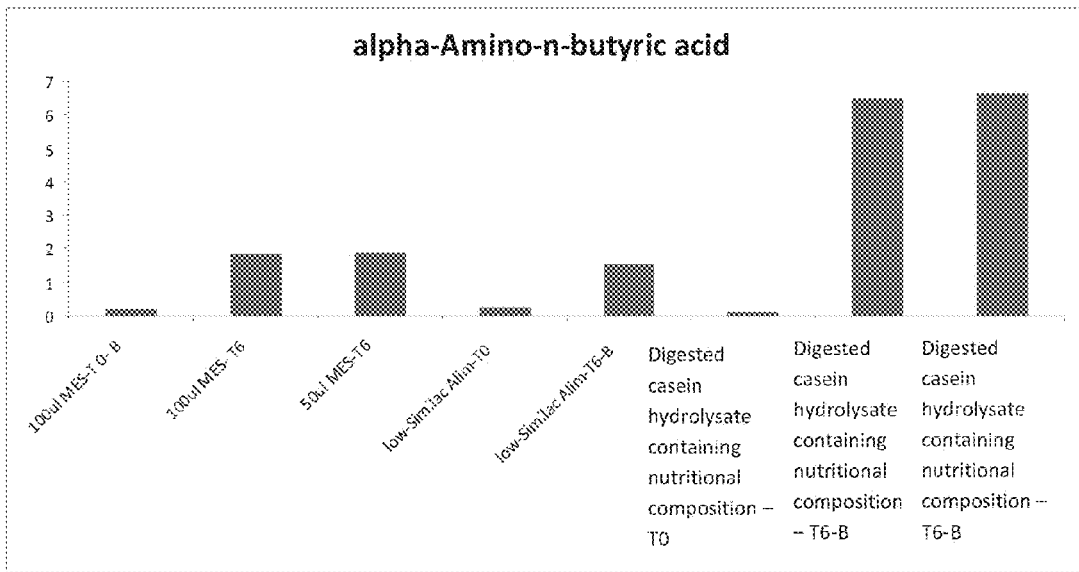
FIG. 10. Concentration (microgram/ml) of alpha-amino-n-butyric acid at T=0 and T=6 of the fecal fermentation experiments with digested (thus >500 Da) Alimentum Similac and a casein hydrolysate-containing nutritional composition of the present disclosure products added at low concentration. Control conditions with MES buffer.

FIG. 10 shows concentration of alpha-amino-n-butyric acid (microgram/ml) at T=0 and T=6 of the fecal fermentation experiments with digested (thus >500 Da), product Alimentum Similac and casein hydrolysate-containing nutritional compositions of the present disclosure added at low concentration. Control conditions with MES buffer. The casein hydrolysate-containing nutritional compositions of the present disclosure stimulated the production of alpha-amino-n-butyric acid during fermentation to a much larger extent than Similac.

Figure 11:
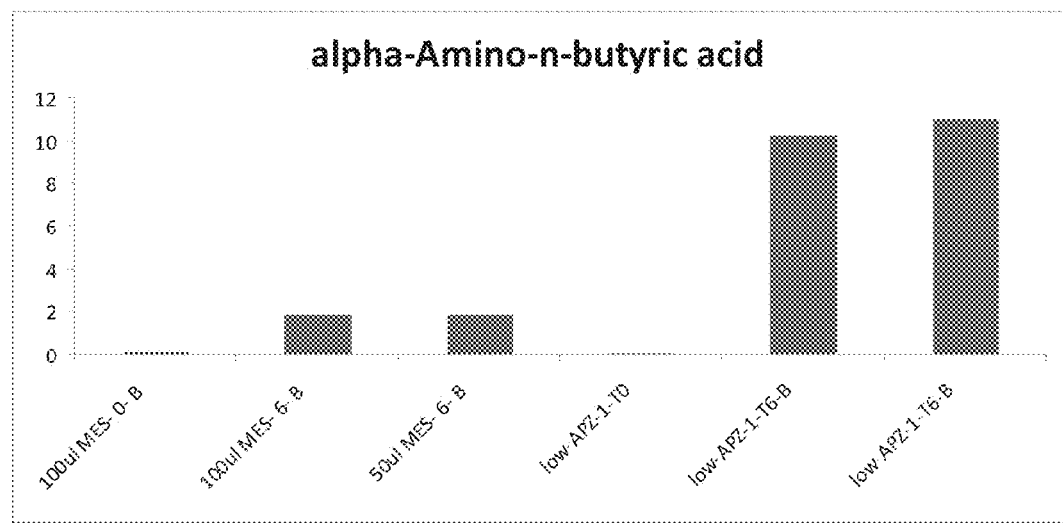
FIG. 11. Concentration (microgram/ml) of alpha-amino-n-butyric acid at T=0 and T=6 of the fecal fermentation experiments with a digested (thus >500 Da) casein hydrolysate of the present disclosure (APZ-1) added at low concentration. Control conditions with MES buffer.

FIG. 11 shows the concentration of alpha-amino-n-butyric acid (microgram/ml) at T=0 and T=6 of the fecal fermentation experiments with digested (thus >500 Da) casein hydrolysate of the present disclosure (APZ-1) added at low concentration. Control conditions with MES buffer. These results strongly indicate the hydrolysate/peptide fraction to contribute to the effects of the casein hydrolysate-containing nutritional compositions.

Figure 12:
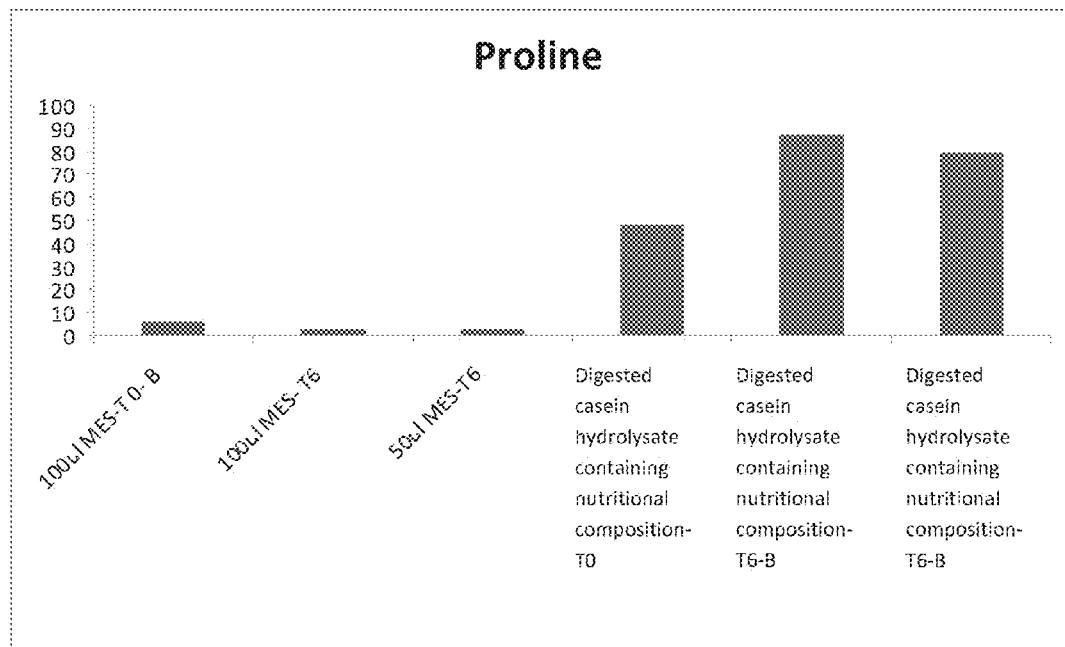
FIG. 12. Concentration (microgram/ml) of proline at T=0 and T=6 of the fecal fermentation experiments with a digested (thus >500 Da) casein hydrolysate-containing nutritional composition of the present disclosure added at low concentration. Control conditions with MES buffer.

FIG. 12 shows the concentration of proline (microgram/ml) at T=0 and T=6 of the fecal fermentation experiments with a digested (thus >500 Da) a casein hydrolysate-containing nutritional composition of the present disclosure added at low concentration. Control conditions with MES buffer. The casein hydrolysate-containing nutritional composition of the present disclosure stimulated proline production during the fermentation.

Figure 13:
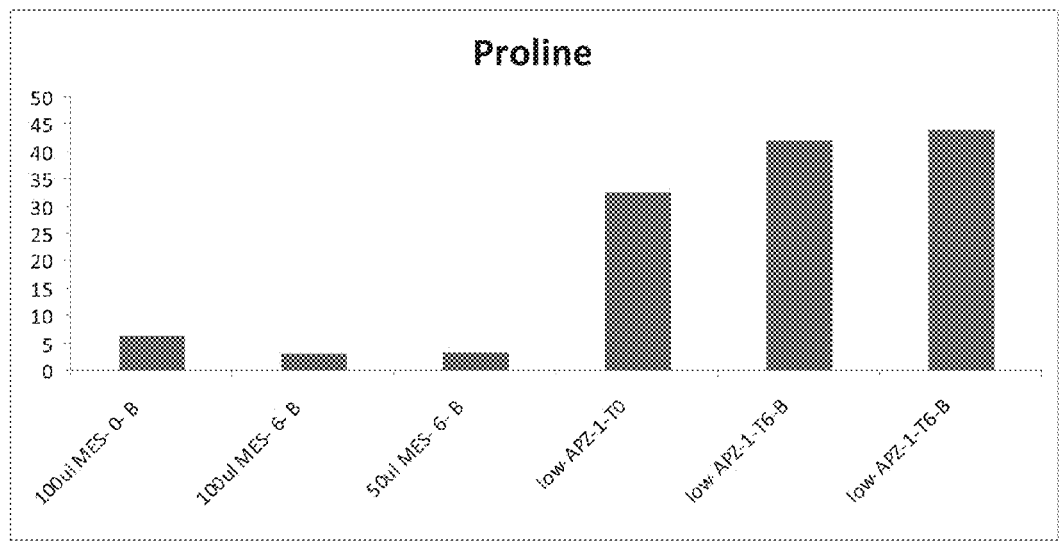
FIG. 13. Concentration (microgram/ml) of proline at T=0 and T=6 of the fecal fermentation experiments with a digested (thus >500 Da) casein hydrolysate of the present disclosure (APZ-1) added at low concentration. Control conditions with MES buffer.

FIG. 13 shows the concentration of proline (microgram/ml) at T=0 and T=6 of the fecal fermentation experiments with a digested (thus >500 Da) a casein hydrolysate of the present disclosure (APZ-1) added at low concentration. Control conditions with MES buffer. These results strongly suggest the hydrolysate/peptide fraction to be involved in the proline stimulating effect of casein hydrolysate-containing nutritional compositions of the present disclosure.

Fermentation of a casein hydrolysate-containing nutritional composition of the present disclosure and a casein hydrolysate and amino acid containing nutritional composition of the present disclosure led to stronger increase in hydroxyproline than other products, whereas lysine was less depleted.

Figure 14:
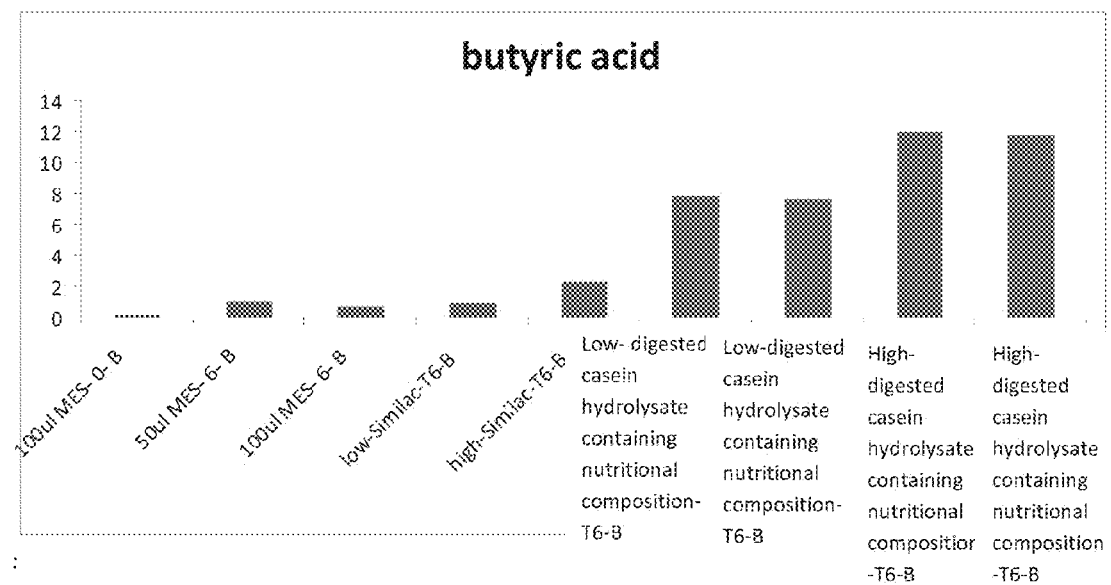
FIG. 14. Concentrations (microgram/ml) of butyric acid at T=6 of the fecal fermentation experiments with digested (thus >500 Da) Alimentum Similac and a casein hydrolysate-containing formula of the present disclosure added at low (9.5 mg/ml) and high concentrations (19 mg/ml). Control conditions with MES buffer.

FIG. 14 shows the concentrations (microgram/ml) of butyric acid at T=6 of the fecal fermentation experiments with digested (thus >500 Da) Alimentum Similac and casein hydrolysate-containing nutritional compositions of the present disclosure added at low (9.5 mg/ml) and high concentrations (19 mg/ml). Control conditions with MES buffer. The casein hydrolysate-containing nutritional compositions of the present disclosure led to an increased production of butyrate as compared to Similac.

Figure 15:
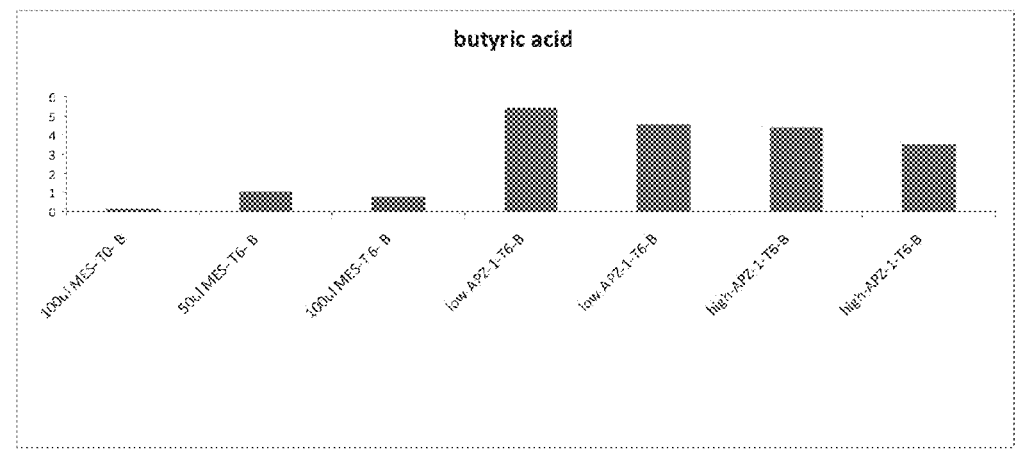
FIG. 15. Concentrations (microgram/ml) of butyric acid at T=6 of the fecal fermentation experiments with a digested (thus >500 Da) casein hydrolysate of the present disclosure (APZ-1) added at low (9.5 mg/ml) and high concentration (19 mg/ml). Control conditions with MES buffer.

FIG. 15 shows the concentrations (microgram/ml) of butyric acid at T=6 of the fecal fermentation experiments with digested (thus >500 Da) a casein hydrolysate of the present disclosure (APZ-1) added at low (9.5 mg/ml) and high concentration (19 mg/ml). Control conditions with MES buffer. These results indicate the hydrolysate/peptides present in the finished product to contribute to the effects on butyrate production.

The highest production of butyrate was observed in the fermentations with a casein hydrolysate-containing nutritional compositions of the present disclosure as compared to other products, also reflected in the highest ratio of butyrate:(acetate+propionate).

In the fermentation experiments casein hydrolysate-containing nutritional compositions of the present disclosure was found to be superior to other products in stimulation a variety of aminoacids (glutamate, threonine) and short chain fatty acids, esp. butyric acid.

Stimulation of CCK

A casein hydrolysate of the present disclosure hydrolysate, as compared with a partial hydrolysate (e.g., Gentlease) or free amino acids was found to stimulate CCK release from STC-1 (intestinal endocrine cell line). Moreover, specific peptides from a casein hydrolysate of the present disclosure may stimulate CCK release form STC-1 cells (DISLLDAQSAPLR, ALPMHIR, GPVRGPFP) These findings may be translated into a potential satiety and gastrointestinal motility supporting effect.

Animal Model (NOD Mouse)

A casein hydrolysate-containing nutritional composition of the present disclosure and a casein hydrolysate of the present disclosure reduce the incidence of T1D in experimental animal models (NOD mouse and DP-BB rat models respectively).

What is claimed is:

1. A method for reducing the risk of type 1 diabetes, treating type 1 diabetes and/or reducing the symptoms of type 1 diabetes, in a subject by administering a composition comprising a casein hydrolysate to the subject, wherein the hydrolysate comprises peptides with a molecular weight of 500 Da to 2000 Da, and wherein the hydrolysate comprises the following peptides: SEQ ID NO. 1, SEQ ID NO. 3, SEQ NO. 4, SEQ ID NO. 7, SEQ ID NO. 9, SEQ ID NO. 12, SEQ ID NO. 16, SEQ ID NO. 18, SEQ ID NO. 20, SEQ ID NO. 23, SEQ ID NO. 27, SEQ ID NO. 31, SEQ ID NO. 33, SEQ ID NO. 34, SEQ ID NO. 35, SEQ ID NO. 39, SEQ ID NO. 40, SEQ ID NO. 44, SEQ ID NO. 47, SEQ ID NO. 48, SEQ ID NO. 49, SEQ ID NO. 50, SEQ ID NO. 57, SEQ ID NO. 59, SEQ ID NO. 62, SEQ ID NO. 65, SEQ ID NO. 66, SEQ ID NO. 67, and SEQ ID NO. 68.

2. The method according to claim 1, wherein the hydrolysate further comprises at least five peptides selected from the group consisting of SEQ ID NO. 2, SEQ ID NO. 5, SEQ ID NO. 6, SEQ ID NO. 8, SEQ ID NO. 10, SEQ ID NO. 11, SEQ ID NO. 13, SEQ ID NO. 14, SEQ ID NO. 15, SEQ ID NO. 17, SEQ ID NO. 19, and SEQ ID NO. 21.

3. The method according to claim 1, wherein the hydrolysate further comprises at least five peptides selected from the group consisting of SEQ ID NO. 22, SEQ ID NO. 24, SEQ ID NO. 25, SEQ ID NO. 26, SEQ ID NO. 28, SEQ ID NO. 29, SEQ ID NO. 30, SEQ ID NO. 32, SEQ ID NO. 36, SEQ ID NO. 37, and SEQ ID NO. 38.

4. The method according to claim 1, wherein the hydrolysate further comprises at least five peptides selected from the group consisting of SEQ ID NO. 41, SEQ ID NO. 42, SEQ ID NO. 43, SEQ ID NO. 45, SEQ ID NO. 46, SEQ ID NO. 51, SEQ ID NO. 52, SEQ ID NO. 53, SEQ ID NO. 54, SEQ ID NO. 55, SEQ ID NO. 56, SEQ ID NO. 58, SEQ ID NO. 60, SEQ ID NO. 61, SEQ ID NO. 63, and SEQ ID NO. 64.

5. The method according to claim 1, wherein the hydrolysate is administered in a nutritional composition, comprising a lipid a fat phase, and a protein source.

6. the method according to claim 5, wherein the nutritional composition comprises about 0.1 to about 1 g/100 kcal of a prebiotic composition, wherein the prebiotic composition comprises at least 20% of an oligosaccharide.

7. The method according to claim 5, wherein the nutritional composition further comprises about 5 to 100 mg/100 kcal of a source of long chain polyunsaturated fatty acids which comprises docosahexanoic acid.

8. The method according to claim 5, wherein the nutritional composition further comprises arachidonic acid.

9. The method according to claim 1, wherein the subject is a human child or juvenile.

10. The method according to claim 5, wherein the nutritional formulation additionally comprises one or more of carbohydrates, nucleic acids, lipids, minerals, anabolic nutrients, vitamins, antioxidants, probiotic bacterial strains and lipotropic agents.

* * * * *